US008188174B2

(12) United States Patent
Cruse et al.

(10) Patent No.: US 8,188,174 B2
(45) Date of Patent: *May 29, 2012

(54) SILATED CORE POLYSULFIDES, THEIR PREPARATION AND USE IN FILLED ELASTOMER COMPOSITIONS

(75) Inventors: Richard W. Cruse, Yorktown Heights, NY (US); W. Michael York, Concord, NC (US); Eric R. Pohl, Mt. Kisco, NY (US); Antonio Chaves, Chappaqua, NY (US); Prashant Joshi, Gaithersburg, MD (US)

(73) Assignee: Momentive Performance Materials Inc., Albany, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/702,971

(22) Filed: Feb. 9, 2010

(65) Prior Publication Data
US 2010/0179279 A1  Jul. 15, 2010

Related U.S. Application Data

(63) Continuation of application No. 11/648,287, filed on Dec. 28, 2006, now Pat. No. 7,696,269.

(51) Int. Cl.
B60C 1/00 (2006.01)
C08K 5/24 (2006.01)
C08K 3/34 (2006.01)

(52) U.S. Cl. ............... 524/262; 524/493; 524/261
(58) Field of Classification Search .......... 524/262, 524/261, 493
See application file for complete search history.

(56) References Cited

U.S. PATENT DOCUMENTS

| | | |
|---|---|---|
| 3,505,166 A | 4/1970 | Jones et al. |
| 3,624,160 A | 11/1971 | Jones et al. |
| 3,692,812 A | 9/1972 | Berger |
| 3,798,196 A | 3/1974 | Rocktaschel et al. |
| 3,842,111 A | 10/1974 | Meyer-Simon et al. |
| 3,869,340 A | 3/1975 | Kotzsch et al. |
| 3,873,489 A | 3/1975 | Thurn et al. |
| 3,922,436 A | 11/1975 | Bell et al. |
| 3,946,059 A | 3/1976 | Janssen et al. |
| 3,957,718 A | 5/1976 | Pochert et al. |
| 3,978,103 A | 8/1976 | Meyer-Simon et al. |
| 3,997,356 A | 12/1976 | Thurn et al. |
| 3,997,581 A | 12/1976 | Pletka et al. |
| 4,044,037 A | 8/1977 | Mui et al. |
| 4,060,539 A | 11/1977 | Seller et al. |
| 4,072,701 A | 2/1978 | Pletka et al. |
| 4,076,550 A | 2/1978 | Thurn et al. |
| 4,099,981 A | 7/1978 | Mui et al. |
| 4,100,172 A | 7/1978 | Mui et al. |
| 4,113,696 A | 9/1978 | Willliams et al. |
| 4,125,552 A | 11/1978 | Speier |
| 4,128,438 A | 12/1978 | Wolff et al. |
| 4,129,585 A | 12/1978 | Buder et al. |
| 4,152,347 A | 5/1979 | Pletka |
| 4,184,998 A | 1/1980 | Shippy et al. |
| 4,210,459 A | 7/1980 | Williams et al. |
| 4,222,915 A | 9/1980 | Wolfff et al. |
| 4,229,333 A | 10/1980 | Wolff et al. |
| 4,375,988 A | 3/1983 | Mueller et al. |
| 4,384,132 A | 5/1983 | Schwarz et al. |
| 4,408,064 A | 10/1983 | Schwarz et al. |
| 4,444,936 A | 4/1984 | Schwarz et al. |
| 4,507,490 A | 3/1985 | Panster et al. |
| 4,514,231 A | 4/1985 | Kerner et al. |
| 4,517,336 A | 5/1985 | Wolff et al. |
| 4,519,430 A | 5/1985 | Ahmad et al. |
| 4,524,169 A | 6/1985 | Wolff et al. |
| 4,574,133 A | 3/1986 | Umpleby |
| 4,704,414 A | 11/1987 | Kerner et al. |
| 4,709,065 A | 11/1987 | Yoshioka et al. |
| 4,820,751 A | 4/1989 | Takeshita et al. |
| 4,959,153 A | 9/1990 | Bradshaw et al. |
| 4,981,937 A | 1/1991 | Kuriyama et al. |
| 5,037,872 A | 8/1991 | Schwarze et al. |
| 5,110,969 A | 5/1992 | Dittrich et al. |
| 5,116,886 A | 5/1992 | Wolff et al. |
| 5,159,009 A | 10/1992 | Wolff et al. |
| 5,399,739 A | 3/1995 | French et al. |
| 5,401,789 A | 3/1995 | Wolff et al. |
| 5,405,985 A | 4/1995 | Parker et al. |
| 5,466,848 A | 11/1995 | Childress |
| 5,468,893 A | 11/1995 | Parker et al. |
| 5,489,701 A | 2/1996 | Childress et al. |
| 5,596,116 A | 1/1997 | Childress et al. |
| 5,605,951 A | 2/1997 | Sandstrom et al. |

(Continued)

FOREIGN PATENT DOCUMENTS

AU  1997/10082  1/1997

(Continued)

OTHER PUBLICATIONS

Abstract for Japanese Pat. Appl. Publ. No. 2001-226383. A published Aug. 21, 2001 (Patent Abstracts for Japan, 1 page) (corresp. To FP2 on attached PTO/SB/08a form).
XP 002479646, Dec. 3, 1996, Takahashi.
XP 002479812, Nov. 20, 2011, Chem. Abstract.
Abstract for Japanese Pat. Appl. Publ. No. 2001-226532A published Aug. 21, 2001 (Patent Abstracts for Japan, 1 page) (corresp. to FP3 on attached PTO/SB/08a form).
Harris, et al., "Ruthenium-catalysed ortho alkylation of hydroxyacetophenones; the functionalisation of ring C aromatic diterpenoids;" Journal of Organometallic Chemistry, 530 (1997) 211-223.
International Search Report PCT/US2007/026294 and Written Opinion.

*Primary Examiner* — Mark Eashoo
*Assistant Examiner* — Angela C Scott
(74) *Attorney, Agent, or Firm* — Dominick G. Vicari; Joseph S. Ostroff

(57) ABSTRACT

This invention relates to novel sulfur-containing silane coupling agents, and organic polymers containing carbon-carbon double bonds. These novel silanes can be carried on organic and inorganic fillers. The invention also relates to articles of manufacture, particularly tires, made from the elastomer compositions described herein.

28 Claims, 1 Drawing Sheet

U.S. PATENT DOCUMENTS

| | | |
|---|---|---|
| 5,650,457 A | 7/1997 | Scholl et al. |
| 5,663,226 A | 9/1997 | Scholl et al. |
| 5,663,358 A | 9/1997 | Cohen et al. |
| 5,663,395 A | 9/1997 | Gobel et al. |
| 5,663,396 A | 9/1997 | Musleve et al. |
| 5,672,639 A | 9/1997 | Corvasce et al. |
| 5,674,932 A | 10/1997 | Agostini et al. |
| 5,675,014 A | 10/1997 | Cohen et al. |
| 5,679,728 A | 10/1997 | Kawazura et al. |
| 5,684,172 A | 11/1997 | Wideman |
| 5,698,619 A | 12/1997 | Cohen et al. |
| 5,719,207 A | 2/1998 | Cohen et al. |
| 5,723,529 A | 3/1998 | Bernard et al. |
| 5,728,778 A | 3/1998 | D'Sidocky et al. |
| 5,733,963 A | 3/1998 | Sandstrom et al. |
| 5,753,732 A | 5/1998 | Wideman et al. |
| 5,770,754 A | 6/1998 | Scholl |
| 5,780,531 A | 7/1998 | Scholl |
| 5,817,852 A | 10/1998 | Ichinohe |
| 5,827,912 A | 10/1998 | Scholl |
| 5,859,275 A | 1/1999 | Munzenberg et al. |
| 5,977,225 A | 11/1999 | Scholl |
| 6,046,349 A | 4/2000 | Batz-Sohn et al. |
| 6,127,468 A | 10/2000 | Cruse et al. |
| 6,140,393 A | 10/2000 | Bomai et al. |
| 6,140,524 A | 10/2000 | Ichonoke et al. |
| 6,194,594 B1 | 2/2001 | Gori et al. |
| 6,194,595 B1 | 2/2001 | Michel et al. |
| 6,204,339 B1 | 3/2001 | Waldman et al. |
| 6,211,345 B1 | 4/2001 | Weller |
| 6,268,421 B1 | 7/2001 | Dittrich et al. |
| 6,359,046 B1 | 3/2002 | Cruse |
| 6,407,153 B1 | 6/2002 | Von Hellens |
| 6,414,061 B1 | 7/2002 | Cruse et al. |
| 6,420,488 B1 | 7/2002 | Penot |
| 6,518,367 B1 | 2/2003 | Yatsuyanagi et al. |
| 6,528,673 B2 | 3/2003 | Cruse et al. |
| 6,608,125 B2 | 8/2003 | Cruse et al. |
| 6,649,684 B1 | 11/2003 | Okel |
| 6,683,135 B2 | 1/2004 | Cruse et al. |
| 6,759,545 B2 | 7/2004 | Yanagisawa et al. |
| 6,777,569 B1 | 8/2004 | Westmeyer et al. |
| 6,849,754 B2 | 2/2005 | Deschler et al. |
| 6,890,981 B1 | 5/2005 | Luginsland |
| 6,984,689 B2 | 1/2006 | Penot et al. |
| 6,984,711 B2 | 1/2006 | Wonmun et al. |
| 7,041,843 B2 | 5/2006 | Yanagisawa et al. |
| 7,122,590 B2 | 10/2006 | Cruse et al. |
| 7,138,537 B2 | 11/2006 | Cruse et al. |
| 7,166,735 B2 | 1/2007 | Yanagisawa et al. |
| 7,186,768 B2 | 3/2007 | Korth et al. |
| 7,199,256 B2 | 4/2007 | Yanagisawa et al. |
| 7,217,751 B2 | 5/2007 | Durel et al. |
| 7,288,667 B2 | 10/2007 | Yanagisawa |
| 7,301,042 B2 | 11/2007 | Cruse |
| 7,307,121 B2 | 12/2007 | Zhang et al. |
| 7,309,797 B2 | 12/2007 | Yanagisawa |
| 7,355,059 B2 | 4/2008 | Yanagisawa |
| 7,368,588 B2 | 5/2008 | Yanagisawa |
| 2002/0002220 A1 | 1/2002 | Reedy et al. |
| 2002/0055564 A1 | 5/2002 | Cruse et al. |
| 2003/0130388 A1 | 7/2003 | Luginsland et al. |
| 2003/0199619 A1 | 10/2003 | Cruse |
| 2003/0200900 A1 | 10/2003 | Korth et al. |
| 2003/0225195 A1 | 12/2003 | Cruse et al. |
| 2004/0143037 A1 | 7/2004 | Chang et al. |
| 2004/0147651 A1 | 7/2004 | Barruel et al. |
| 2004/0210001 A1 | 10/2004 | Cruse et al. |
| 2004/0220307 A1 | 11/2004 | Wu |
| 2005/0009955 A1 | 1/2005 | Cohen |
| 2005/0027060 A1 | 2/2005 | Yagi et al. |
| 2005/0176861 A1 | 8/2005 | Nakayama et al. |
| 2005/0245753 A1 | 11/2005 | Cruse et al. |
| 2005/0245754 A1 | 11/2005 | Glatzer et al. |
| 2006/0036034 A1 | 2/2006 | Chaves et al. |
| 2006/0106143 A1 | 5/2006 | Lin et al. |
| 2006/0177657 A1 | 8/2006 | Weller |
| 2006/0205907 A1 | 9/2006 | Guyer |
| 2006/0235236 A1 | 10/2006 | Simandan |
| 2006/0281841 A1 | 12/2006 | Weller et al. |
| 2007/0037915 A1 | 2/2007 | Masumoto |
| 2007/0135572 A1 | 6/2007 | Wolter |
| 2007/0197812 A1 | 8/2007 | Chaves et al. |
| 2007/0197813 A1 | 8/2007 | Chaves et al. |
| 2008/0027162 A1 | 1/2008 | Hua et al. |
| 2008/0161452 A1 | 7/2008 | York et al. |
| 2008/0161459 A1 | 7/2008 | Cruse et al. |
| 2008/0161460 A1 | 7/2008 | York et al. |
| 2008/0161461 A1 | 7/2008 | Cruse et al. |
| 2008/0161462 A1 | 7/2008 | York et al. |
| 2008/0161463 A1 | 7/2008 | Cruse et al. |
| 2008/0161475 A1 | 7/2008 | York et al. |
| 2008/0161486 A1 | 7/2008 | York et al. |
| 2008/0161590 A1 | 7/2008 | Cruse et al. |

FOREIGN PATENT DOCUMENTS

| | | |
|---|---|---|
| CA | 991836 | 6/1976 |
| CA | 1018991 | 10/1977 |
| CA | 2103653 | 2/1994 |
| CA | 2186060 | 3/1997 |
| CA | 2231302 | 9/1998 |
| CA | 2146333 | 5/2010 |
| DE | 2141159 | 3/1973 |
| DE | 2141160 | 3/1973 |
| DE | 2255577 | 6/1974 |
| DE | 2360471 | 6/1975 |
| DE | 2405758 | 8/1975 |
| DE | 2536674 | 2/1977 |
| DE | 2747277 | 4/1979 |
| DE | 2819638 | 11/1979 |
| DE | 2848559 | 5/1980 |
| DE | 2856229 | 7/1980 |
| DE | 3028365 | 2/1982 |
| DE | 3305373 | 8/1984 |
| DE | 3314742 | 10/1984 |
| DE | 3311340 | 11/1984 |
| DE | 3437473 | 4/1986 |
| DE | 4023537 | 1/1992 |
| DE | 4119959 | 12/1992 |
| DE | 4128203 | 5/1993 |
| DE | 4236218 | 6/1993 |
| DE | 4225978 | 4/1994 |
| DE | 43088311 | 9/1994 |
| DE | 19702046 | 1/1998 |
| DE | 19819373 | 11/1999 |
| DE | 10222509 | 3/2003 |
| DE | 4004781 | 5/2010 |
| EP | 0784072 | 7/1977 |
| EP | 0845493 | 6/1996 |
| EP | 0764687 | 3/1997 |
| EP | 0795577 | 9/1997 |
| EP | 0845493 | 6/1998 |
| EP | 0680997 | 9/1998 |
| EP | 0864605 | 9/1998 |
| EP | 0732362 | 6/1999 |
| EP | 0773224 | 12/2001 |
| EP | 0631982 | 1/2002 |
| EP | 0955302 | 6/2002 |
| EP | 0919559 | 11/2002 |
| EP | 0848006 | 8/2003 |
| EP | 1491545 | 12/2004 |
| EP | 0738748 | 8/2005 |
| EP | 1270657 | 3/2006 |
| EP | 1634726 | 3/2006 |
| EP | 1514892 | 7/2006 |
| EP | 1714984 | 10/2006 |
| FR | 2804104 | 7/2001 |
| GB | 1439247 | 6/1976 |
| GB | 2259303 | 10/1993 |
| JP | 63-270751 | 8/1988 |
| JP | 8319225 | 12/1996 |
| JP | 2000-154380 | 6/2000 |
| JP | 2001-226383 | 8/2001 |
| JP | 2001-226532 | 8/2001 |
| JP | 2005-263127 | 9/2005 |
| JP | 2005-263998 | 9/2005 |
| JP | 2005-263999 | 9/2005 |

| | | |
|---|---|---|
| JP | 2005-272630 | 10/2005 |
| JP | 2005-281621 | 10/2005 |
| JP | 2005-320317 | 11/2005 |
| JP | 2005-320374 | 11/2005 |
| JP | 2006-28245 | 2/2006 |
| JP | 2006-28253 | 2/2006 |
| JP | 2006-28430 | 2/2006 |
| JP | 2006-104455 | 4/2006 |
| JP | 2006-213777 | 8/2006 |
| JP | 2006-213803 | 8/2006 |
| JP | 2006-225448 | 8/2006 |
| JP | 2006-232881 | 9/2006 |
| JP | 2006-232916 | 9/2006 |
| JP | 2006-232917 | 9/2006 |
| JP | 2007-51169 | 3/2007 |
| KR | 10-2005-0025817 | 3/2005 |
| WO | 98/53004 | 11/1998 |
| WO | 99/07713 | 2/1999 |
| WO | 99/09036 | 2/1999 |
| WO | 00/05300 | 2/2000 |
| WO | 00/53671 | 9/2000 |
| WO | 01/46202 | 6/2001 |
| WO | 02/20534 | 3/2002 |
| WO | 02/48256 | 6/2002 |
| WO | 03/035252 | 5/2003 |
| WO | 2004000930 | 12/2003 |
| WO | 2004/005395 | 1/2004 |
| WO | 2005/007660 | 1/2005 |
| WO | 2005/007661 | 1/2005 |
| WO | 2006/113122 | 10/2006 |
| WO | 2007/039416 | 4/2007 |
| WO | 2007/068555 | 6/2007 |
| WO | 2007/085521 | 8/2007 |
| WO | 2007/132909 | 11/2007 |
| WO | 2008/074567 | 6/2008 |

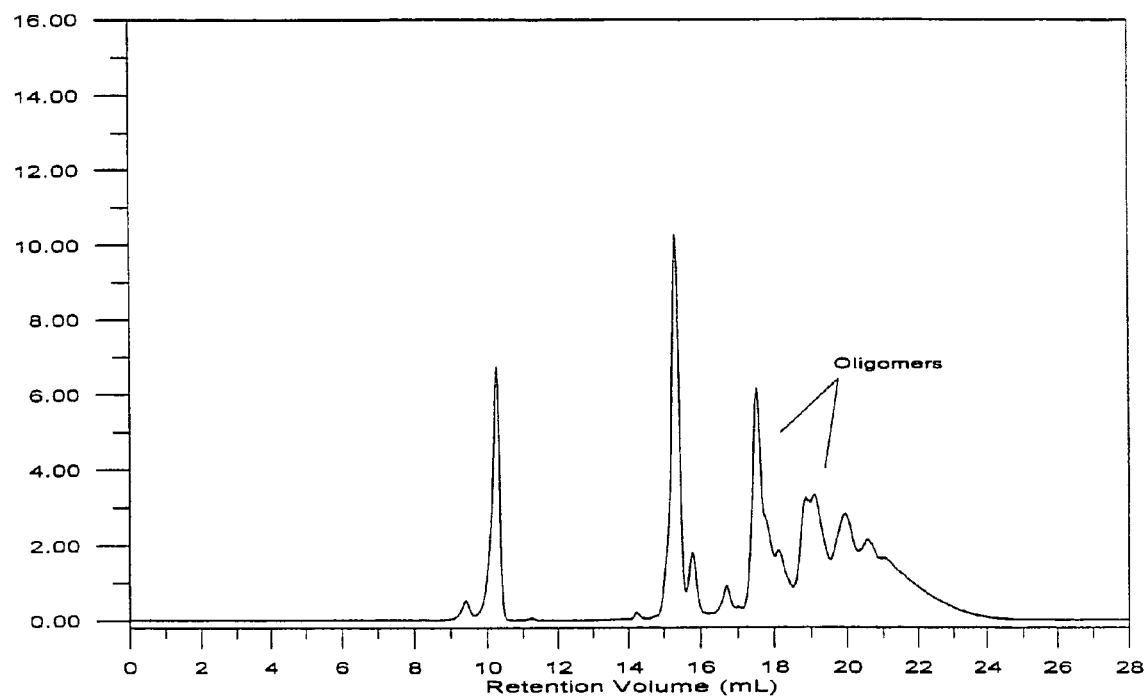

SILATED CORE POLYSULFIDES, THEIR PREPARATION AND USE IN FILLED ELASTOMER COMPOSITIONS

CROSS-REFERENCE TO RELATED APPLICATIONS

The present application is a continuation of U.S. application Ser. No. 11/648,287 filed Dec. 28, 2006, now U.S. Pat. No. 7,696,269, to which priority is claimed.

The present application is directed to an invention which was developed pursuant to a joint research agreement wherein the meaning of 35 U.S.C. §103(c). The joint research agreement dated May 7, 2001 as amended, between Continental AG, and General Electric Company, on behalf of GE Advanced Materials, Silicones Division, now Momentive Performance Materials Inc.

The present application is related to the following applications, filed on even date herewith, with the disclosures of each the applications being incorporated by reference herein in their entireties:

Application Ser. No. 11/617,683, filed on Dec. 28, 2006, entitled "Tire Compositions And Components Containing Silated Cyclic Core Polysulfides".

Application Ser. No. 11/617,649, filed on Dec. 28, 2006, entitled "Tire Compositions And Components Containing Free-Flowing Filler Compositions".

Application Ser. No. 11/617,678, filed on Dec. 28, 2006, entitled "Tire Compositions And Components Containing Free-Flowing Filler Compositions".

Application Ser. No. 11/617,663, filed on Dec. 28, 2006, entitled "Tire Compositions And Components Containing Silated Core Polysulfides".

Application Ser. No. 11/617,659, filed on Dec. 28, 2006, entitled "Tire Compositions And Components Containing Blocked Mercaptosilane Coupling Agent".

Application Ser. No. 11/647,901, filed on Dec. 28, 2006, entitled "Silated Cyclic Core Polysulfides, Their Preparation And Use In Filled Elastomer Compositions".

Application Ser. No. 11/647,460, filed on Dec. 28, 2006, entitled "Free-Flowing Filler Composition And Rubber Composition Containing Same".

Application Ser. No. 11/647,903, filed on Dec. 28, 2006, entitled "Free-Flowing Filler Composition And Rubber Composition Containing Same".

Application Ser. No. 11/647,780, filed on Dec. 28, 2006, entitled "Blocked Mercaptosilane Coupling Agents, Process For Making And Uses In Rubber".

FIELD OF THE INVENTION

The present invention generally relates to silated core polysulfides compositions, process for their preparation, and rubber compositions comprising same.

BACKGROUND OF THE INVENTION

Sulfur-containing coupling agents used for mineral-filled elastomers involve silanes in which two alkoxysilylalkyl groups are bound, each to one end of a chain of sulfur atoms. The two alkoxysilyl groups are bonded to the chain of sulfur atoms by two similar, and in most cases, identical, hydrocarbon fragments. The general silane structures just described, hereinafter referred to as "simple bis polysulfide silanes," usually contain a chain of three methylene groups as the two mediating hydrocarbon units. In some cases, the methylene chain is shorter, containing only one or two methylenes per chain. The use of these compounds is primarily as coupling agents for mineral-filled elastomers. These coupling agents function by chemically bonding silica or other mineral fillers to polymer when used in rubber applications. Coupling is accomplished by chemical bond formation between the silane sulfur and the polymer and by hydrolysis of the alkoxysilyl groups and subsequent condensation with silica hydroxyl groups. The reaction of the silane sulfur with the polymer occurs when the S—S bonds are broken and the resulting fragment adds to the polymer. A single linkage to the polymer occurs for each silyl group bonded to the silica. This linkage contains a single, relatively weak C—S and/or S—S bond(s) that forms the weak link between the polymer and the silica. Under high stress, this single C—S and/or S—S linkages may break and therefore contribute to wear of the filled elastomer.

The use of polysulfide silanes coupling agents in the preparation of rubber is well known. These silanes contain two silicon atoms, each of which is bound to a disubstituted hydrocarbon group, and three other groups of which at least one is removable from silicon by hydrolysis. Two such hydrocarbon groups, each with their bound silyl group, are further bound to each end of a chain of at least two sulfur atoms. These structures thus contain two silicon atoms and a single, continuous chain of sulfur atoms of variable length.

Hydrocarbon core polysulfide silanes that feature a central molecular core isolated from the silicon in the molecule by sulfur-sulfur bonds are known in the art. Polysufide silanes containing a core that is an aminoalkyl group separated from the silicon atom by a single sulfur and a polysulfide group and where the polysulfide group is bonded to the core at a secondary carbon atom are also know in the art. As well as core fragments in which only two polysulfide groups are attached to the core.

When the polysulfide groups are attached directly to an aromatic core, the reactivity with the polymer (rubber) is reduced. The aromatic core is sterically bulky which inhibits the reaction. Compositions in which the polysulfides are attached directly to cyclic aliphatic fragments derived by vinyl cyclohexene contain more than one silated core and form large rings. The cyclohexyl core is sterically more hindered than the aromatic core and is less reactive. Although these compositions can form more than one sulfur linkage to the polymer rubber for each attachment of the coupling agent to the silica through the silyl group, their effectiveness is low due to the low reactivity.

The low reactivity is due to the attachment of the polysulfide to the secondary carbon of cyclic core structure. The positioning of the polysulfide group is not optimal for reaction with the accelerators and reaction with the polymer.

The present invention overcomes the deficiencies of the aforementioned compositions involving silane coupling agents in several ways. The silanes of the present invention described herein are not limited to two silyl groups nor to one chain of sulfur atoms. In fact the molecular architecture in which multiple polysulfide chains are oriented in a noncollinear configuration (i.e. branched, in the sense that the branch points occur within the carbon backbone interconnecting the polysulfide chains) is novel.

The silanes of the present invention have advantages over that in the prior art by providing a means to multiple points of sulfur attachment to polymer per point of silicon attachment to filler. The silanes described herein may be asymmetric with regard to the groups on the two ends of the sulfur chains. The silyl groups, rather than occurring at the ends of the molecule, tend to occur more centrally and are chemically bonded to the core through carbon-carbon or carbon-silicon bonds. The core also contains multiple polysulfide groups that are attached to a primary carbon atom. The attachment decreases significantly the steric hinderance of the core, and increases the reactivity of the polysulfides with the polymer. This distinction is what allows silane silicon to become and remain bonded (through the intermediacy of a sequence of covalent chemical bonds) to polymer at multiple points using the silanes of the present invention.

Also, without being bound by theory, silated core silanes of the present invention include a Y-core structure. This Y-core structure is believed to enable bonding the polymer at two different points or crosslinking on two different polymer chains, and also enables attachment, such as by bonding, to a filler.

The examples presented herein demonstrate that the silanes of the present invention impart a desirable balance of physical properties (performance to mineral-filled elastomer compositions) and better wear characteristics to articles manufactured from these elastomers. Improvements in rolling resistance are also apparent for elastomers used in tire applications.

SUMMARY OF THE INVENTION

In a first embodiment of the present invention, novel silated core polysulfides of the general Formula (1)

$$[Y^1R^1S_x-]_m[G^1(R^2SiX^1X^2X^3)_a]_n[G^2]_o[R^3Y^2]_p \qquad (1)$$

is provided, wherein each occurrence of $G^1$ is independently selected from a polyvalent hydrocarbon species having from 1 to about 30 carbon atoms and containing a polysulfide group represented by Formula (2)

$$[(CH_2)_b-]_cR^4[-(CH_2)_dS_x-]_e; \qquad (2)$$

each occurrence of $G^2$ is independently selected from a polyvalent hydrocarbon species of 1 to about 30 carbon atoms and containing a polysulfide group represented by Formula (3)

$$[(CH_2)_b-]_cR^5[-(CH_2)_dS_x-]_e; \qquad (3)$$

each occurrence of $R^1$ and $R^3$ are independently selected from a divalent hydrocarbon fragment having from 1 to about 20 carbon atoms that include branched and straight chain alkyl, alkenyl, alkynyl, aryl or aralkyl groups in which one hydrogen atom was substituted with a $Y^1$ or $Y^2$ group;

each occurrence of $Y^1$ and $Y^2$ is independently selected from, but not limited to silyl ($-SiX^1X^2X^3$), carboxylic acid ($-C(=O)OH$), ester ($-C(=O)OR^6$), in which $R^6$ is any monovalent hydrocarbon group having from 1 to 20 carbon atoms, and includes branched or straight chain alkyl, alkenyl, aryl or aralkyl groups), hydrogen and the like.

each occurrence of $R^2$ is a straight chain hydrocarbon represented by $-(CH_2)_f-$;

each occurrence of $R^4$ is chosen independently from a polyvalent hydrocarbon fragment of 1 to about 28 carbon atom that was obtained by substitution of hydrogen atoms equal to the sum of a+c+e, and include cyclic, branched and straight chain alkyl, alkenyl, alkynyl, aryl and aralkyl groups in which a+c+e−1 hydrogens have been replaced, or a polyvalent heterocarbon fragment from 1 to 27 carbon atoms;

each occurrence of $R^5$ is independently selected from a polyvalent hydrocarbon fragment of 1 to about 28 carbon atom that was obtained by substitution of hydrogen atoms equal to the sum of c+e, and include cyclic, branched and straight chain alkyl, alkenyl, alkynyl, aryl and aralkyl groups in which c+e−1 hydrogens have been replaced, or a polyvalent heterocarbon fragment from 1 to 27 carbon atoms;

each occurrence of $X^1$ is independently selected from hydrolyzable groups consisting of $-Cl$, $-Br$, $-OH$, $-OR^6$, and $R^6C(=O)O-$, wherein $R^6$ is any monovalent hydrocarbon group having from 1 to 20 carbon atoms, and includes branched or straight chain alkyl, alkenyl, aryl or aralkyl groups;

each occurrence of $X^2$ and $X^3$ is independently selected from the group consisting of hydrogen, the members listed above for $R^6$, the members listed above for $X^1$ and $-OSi$ containing groups that result from the condensation of silanols;

each occurrence of the subscripts, a, b, c, d, e, f, m, n, o, p, and x, is independently given by a is 1 to about 3; b is 1 to about 5; c is 1 to about 3; d is 1 to about 5; e is 1 to about 3; f is 0 to about 5; m is 1 to about 100, n is 1 to about 15; o is 0 to about 10; p is 1 to about 100, and x is 1 to about 10.

In a second embodiment of the present invention, a process for the preparation of the silated core polysulfide composition comprising reacting a hydrocarbon or heterocarbon containing vinyl groups with $HSiX^1X^2X^3$, the resultant silylated hydrocarbon or silylated heterocarbon is reacted with a thioacid, the acyl group is removed, and the mercapto groups are reacted with base and sulfur and followed by the reaction of a halo containing hydrocarbon silane is disclosed.

In accordance with a third embodiment of the present invention, a rubber composition is provided comprising (a) a rubber component; (b) an inorganic filler; and a silated core polysulfide composition having the general formula $$[Y^1R^1S_x-]_m[G^1(R^2SiX^1X^2X^3)_a]_n[G^2]_o[R^3Y^2]_p$$

wherein $Y^1$, $R^1S$, $G^1R^2$, $X^1$, $X^2$, $X^3$, $G^2$, $R^3$, $Y^2$, a, o, p, x, m, and n have the aforestated meanings.

The compositions of the present invention exhibit excellent dispersion of filler and can achieve excellent workability, and improved productivity in vulcanization.

BRIEF DESCRIPTION OF THE DRAWING

FIG. 1 shows HPLC analysis of the product of Example 1.

DETAILED DESCRIPTION OF THE PRESENT INVENTION

The novel silated core polysulfides of the present invention are represented by Formula (1)

$$[Y^1R^1S_x-]_m[G^1(R^2SiX^1X^2X^3)_a]_n[G^2]_o[R^3Y^2]_p \qquad \text{(Formula 1)}$$

wherein each occurrence of $G^1$ is independently selected from a polyvalent hydrocarbon species having from 1 to about 30 carbon atoms and containing a polysulfide group represented by Formula (2)

$$[(CH_2)_b-]_cR^4[-(CH_2)_dS_x-]_e; \qquad \text{(Formula 2)}$$

each occurrence of $G^2$ is independently selected from a polyvalent hydrocarbon species of 1 to about 30 carbon atoms and containing a polysulfide group represented by Formula (3)

$$[(CH_2)_b-]_cR^5[-(CH_2)_dS_x-]_e; \qquad \text{(Formula 3)}$$

each occurrence of $R^1$ and $R^3$ are independently selected from a divalent hydrocarbon fragment having from 1 to about 20 carbon atoms that include branched and straight chain alkyl, alkenyl, alkynyl, aryl or aralkyl groups in which one hydrogen atom was substituted with a $Y^1$ or $Y^2$ group;

each occurrence of $Y^1$ and $Y^2$ is independently selected from, but not limited to silyl ($-SiX^1X^2X^3$), carboxylic acid ($-C(=O)OH$), ester ($-C(=O)OR^6$), wherein $R^6$ is a monovalent hydrocarbon group having from 1 to 20 carbon atoms, and includes branched or straight chain alkyl, alkenyl, aryl or aralkyl groups), hydrogen and the like; each occurrence of $R^2$ is a straight chain hydrocarbon represented by $-(CH_2)_f-$; each occurrence of $R^4$ is chosen independently from a polyvalent hydrocarbon fragment of 1 to about 28 carbon atom that was obtained by substitution of hydrogen atoms equal to the sum of a+c+e, and include cyclic, branched and straight chain alkyl, alkenyl, alkynyl, aryl and aralkyl groups in which a+c+e−1 hydrogens have been replaced or a polyvalent heterocarbon fragment from 1 to 27 carbon atoms;

each occurrence of $R^5$ is independently selected from a polyvalent hydrocarbon fragment of 1 to about 28 carbon atom that was obtained by substitution of hydrogen atoms equal to the sum of c+e, and include cyclic, branched and straight chain alkyl, alkenyl, alkynyl, aryl and aralkyl groups in which c+e−1 hydrogens have been replaced or a polyvalent heterocarbon fragment from 1 to 27 carbon atoms;

each occurrence of $X^1$ is independently selected from hydrolyzable groups consisting of $-Cl$, $-Br$, $-OH$, $-OR^6$, and $R^6C(=O)O-$, wherein $R^6$ is any monovalent hydrocarbon group having from 1 to 20 carbon atoms, and includes branched or straight chain alkyl, alkenyl, aryl or aralkyl groups;

each occurrence of $X^2$ and $X^3$ is independently selected from the group consisting of hydrogen, the members listed above for $R^6$, the members listed above for $X^1$ and —OSi containing groups that result from the condensation of silanols;

each occurrence of the subscripts, a, b, c, d, e, f, m, n, o, p, and x, is independently given by a is 1 to about 3; b is 1 to about 5; c is 1 to about 3; d is 1 to about 5; e is 1 to about 3; f is 0 to about 5; m is 1 to about 100, n is 1 to about 15; o is 0 to about 10; p is 1 to about 100, and x is 1 to about 10.

The term, "heterocarbon", as used herein, refers to any hydrocarbon structure in which the carbon-carbon bonding backbone is interrupted by bonding to atoms of nitrogen and/or oxygen, or in which the carbon-carbon bonding backbone is interrupted by bonding to groups of atoms containing sulfur, nitrogen and/or oxygen, such as cyanurate ($C_3N_3$). Heterocarbon fragments also refer to any hydrocarbon in which a hydrogen or two or more hydrogens bonded to carbon are replaced with a sulfur, oxygen or nitrogen atom, such as a primary amine ($-NH_2$), and oxo ($=O$), and the like.

Thus, $R^4$ and $R^5$ include, but are not limited to branched, straight-chain, cyclic, and/or polycyclic polyvalent aliphatic hydrocarbons, optionally containing ether functionality via oxygen atoms each of which is bound to two separate carbon atoms, polysulfide functionality, in which the polysulfide group ($-S_x-$) is bonded to two separate carbon atoms on $G^1$ or $G^2$ to form a ring, tertiary amine functionality via nitrogen atoms each of which is bound to three separate carbon atoms, cyano (CN) groups, and/or cyanurate ($C_3N_3$) groups; aromatic hydrocarbons; and arenes derived by substitution of the aforementioned aromatics with branched or straight chain alkyl, alkenyl, alkynyl, aryl and/or aralkyl groups.

As used herein, "alkyl" includes straight, branched and cyclic alkyl groups; "alkenyl" includes any straight, branched, or cyclic alkenyl group containing one or more carbon-carbon double bonds, where the point of substitution can be either at a carbon-carbon double bond or elsewhere in the group; and "alkynyl" includes any straight, branched, or cyclic alkynyl group containing one or more carbon-carbon triple bonds and optionally also one or more carbon-carbon double bonds as well, where the point of substitution can be either at a carbon-carbon triple bond, a carbon-carbon double bond, or elsewhere in the group. Examples of alkyls include, but are not limited to methyl, ethyl, propyl, isobutyl. Examples of alkenyls include, but are not limited to vinyl, propenyl, allyl, methallyl, ethylidenyl norbornane, ethylidene norbornyl, ethylidenyl norbornene, and ethylidene norbornenyl. Some examples of alkynyls include, but are not limited to acetylenyl, propargyl, and methylacetylenyl.

As used herein, "aryl" includes any aromatic hydrocarbon from which one hydrogen atom has been removed; "aralkyl" includes any of the aforementioned alkyl groups in which one or more hydrogen atoms have been substituted by the same number of like and/or different aryl (as defined herein) substituents; and "arenyl" includes any of the aforementioned aryl groups in which one or more hydrogen atoms have been substituted by the same number of like and/or different alkyl (as defined herein) substituents. Some examples of aryls include, but are not limited to phenyl and naphthalenyl. Examples of aralkyls include, but are not limited to benzyl and phenethyl, and some examples of arenyls include, but are not limited to tolyl and xylyl.

As used herein, "cyclic alkyl", "cyclic alkenyl", and "cyclic alkynyl" also include bicyclic, tricyclic, and higher cyclic structures, as well as the aforementioned cyclic structures further substituted with alkyl, alkenyl, and/or alkynyl groups. Representative examples include, but are not limited to norbornyl, norbornenyl, ethylnorbornyl, ethylnorbornenyl, ethylcyclohexyl, ethylcyclohexenyl, cyclohexylcyclohexyl, and cyclododecatrienyl, and the like.

Representative examples of $X^1$ include, but are not limited to methoxy, ethoxy, propoxy, isopropoxy, butoxy, phenoxy, benzyloxy, hydroxy, chloro, and acetoxy. Representative examples of $X^2$ and $X^3$ include the representative examples listed above for $X^1$ as well as hydrogen, methyl, ethyl, propyl, isopropyl, sec-butyl, phenyl, vinyl, cyclohexyl, and higher straight-chain alkyl, such as butyl, hexyl, octyl, lauryl, and octadecyl.

Representative examples of $R^1$ and $R^3$ include the terminal straight-chain alkyls further substituted terminally at the other end, such as $-CH_2-$, $-CH_2CH_2-$, $-CH_2CH_2CH_2-$, and $-CH_2CH_2CH_2CH_2CH_2CH_2CH_2CH_2-$, and their beta-substituted analogs, such as $-CH_2(CH_2)_uCH(CH_3)-$, where u is zero to 17; the structure derivable from methallyl chloride, $-CH_2CH(CH_3)CH_2-$; any of the structures derivable from divinylbenzene, such as $-CH_2CH_2(C_6H_4)CH_2CH_2-$ and $-CH_2CH_2(C_6H_4)CH(CH_3)-$, where the notation $C_6H_4$ denotes a disubstituted benzene ring; any of the structures derivable from diallylether, such as $-CH_2CH_2CH_2OCH_2CH_2CH_2-$ and $-CH_2CH_2CH_2OCH_2CH(CH_3)-$; any of the structures derivable from butadiene, such as $-CH_2CH_2CH_2CH_2-$, $-CH_2CH_2CH(CH_3)-$, and $-CH_2CH(CH_2CH_3)-$; any of the structures derivable from piperylene, such as $-CH_2CH_2CH_2CH(CH_3)-$, $-CH_2CH_2CH(CH_2CH_3)-$, and $-CH_2CH(CH_2CH_2CH_3)-$; any of the structures derivable from isoprene, such as $-CH_2CH(CH_3)CH_2CH_2-$, $-CH_2CH(CH_3)CH(CH_3)-$, $-CH_2C(CH_3)(CH_2CH_3)-$, $-CH_2CH_2CH(CH_3)CH_2-$, $-CH_2CH_2C(CH_3)_2-$ and $-CH_2CH[CH(CH_3)_2]-$; any of the isomers of $-CH_2CH_2$-norbornyl-, $-CH_2CH_2$-cyclohexyl-; any of the diradicals obtainable from norbornane, cyclohexane, cyclopentane, tetrahydrodicyclopentadiene, or cyclododecene by loss of two hydrogen atoms; the structures derivable from limonene, $-CH_2CH(4\text{-methyl-1-}C_6H_9-)CH_3$, where the notation $C_6H_9$ denotes isomers of the trisubstituted cyclohexane ring lacking substitution in the 2 position; any of the monovinyl-containing structures derivable from trivinylcyclohexane, such as $-CH_2CH_2(vinylC_6H_9)CH_2CH_2-$ and $-CH_2CH_2(vinylC_6H_9)CH(CH_3)-$, where the notation $C_6H_9$ denotes any isomer of the trisubstituted cyclohexane ring; any of the monounsaturated structures derivable from myrcene containing a trisubstituted C=C, such as —CH$_2$CH[CH$_2$CH$_2$CH=C(CH$_3$)$_2$]CH$_2$CH$_2$—, —CH$_2$CH[CH$_2$CH$_2$CH=C(CH$_3$)$_2$]CH(CH$_3$)—, —CH$_2$C[CH$_2$CH$_2$CH=C(CH$_3$)$_2$](CH$_2$CH$_3$)—, —CH$_2$CH$_2$CH[CH$_2$CH$_2$CH=C(CH$_3$)$_2$]CH$_2$—, —CH$_2$CH$_2$(C—)(CH$_3$)[CH$_2$CH$_2$CH=C(CH$_3$)$_2$], and —CH$_2$CH[CH(CH$_3$)[CH$_2$CH$_2$CH=C(CH$_3$)$_2$]]—; and any of the monounsaturated structures derivable from myrcene lacking a trisubstituted C=C, such as —CH$_2$CH(CH=CH$_2$)CH$_2$CH$_2$CH$_2$C(CH$_3$)$_2$—, —CH$_2$CH(CH=CH$_2$)CH$_2$CH$_2$CH[CH(CH$_3$)$_2$]—, —CH$_2$C(=CH—CH$_3$)CH$_2$CH$_2$CH$_2$C(CH$_3$)$_2$—, —CH$_2$C(=CH—CH$_3$)CH$_2$CH$_2$CH[CH(CH$_3$)$_2$]—, —CH$_2$CH$_2$C(=CH$_2$)CH$_2$CH$_2$CH$_2$C(CH$_3$)$_2$—, —CH$_2$CH$_2$C(=CH$_2$)CH$_2$CH$_2$CH[CH(CH$_3$)$_2$]—, —CH$_2$CH=C(CH$_3$)$_2$CH$_2$CH$_2$CH$_2$C(CH$_3$)$_2$—, and —CH$_2$CH=C(CH$_3$)$_2$CH$_2$CH$_2$CH[CH(CH$_3$)$_2$].

Representative examples of tridentate $G^1$ include, but are not limited to, structures derivable from nonconjugated terminal diolefins, such as —CH$_2$(CH$_2$)$_{q+1}$CH(CH$_2$—)— and —CH(CH$_3$)(CH$_2$)$_q$CH(CH$_2$—)$_2$, in which q is zero to 20; any of the structures derivable from divinylbenzene, such as —CH$_2$CH$_2$(C$_6$H$_4$)CH(CH$_2$—)— and —CH$_2$CH$_2$(C$_6$H$_3$—)CH$_2$CH$_2$—, where the notation C$_6$H$_4$ denotes a disubstituted benzene ring and C$_6$H$_3$— denotes a trisubstituted ring; structures derivable from butadiene, such as —CH$_2$(CH—)CH$_2$CH$_2$—; any of the structures derivable from isoprene, such as —CH$_2$(C—)(CH$_3$)CH$_2$CH$_2$— and —CH$_2$CH(CH$_3$)(CH—)CH$_2$—; any structures derivable from trivinylcyclohexane, such as —CH$_2$(CH—)(vinylC$_6$H$_9$)CH$_2$CH$_2$—; (—CH$_2$CH$_2$)$_3$C$_6$H$_9$, and (—CH$_2$CH$_2$)$_2$C$_6$H$_9$CH(CH$_3$)—, where the notation C$_6$H$_9$ denotes any isomer of the trisubstituted cyclohexane ring; any of the structures derivable from myrcene, such as, —CH$_2$(C—)[CH$_2$CH$_2$CH=C(CH$_3$)$_2$]CH$_2$CH$_2$—, and —CH$_2$CH[CH$_2$CH$_2$CH=C(CH$_3$)$_2$](CH—)CH$_2$—; the structures derivable from trimethylolalkanes, such as CH$_3$CH$_2$CH$_2$C(CH$_2$—)$_3$ and CH$_3$CH$_2$C(CH$_2$—)$_3$; glyceryl, whose structure is —CH$_2$(CH—)CH$_2$—, and its methyl analog, whose structure is —CH$_2$(—CCH$_3$)CH$_2$—; and the triethanolamine derivative, (—CH$_2$CH$_2$)$_3$N.

Representative examples of polyvalent $G^1$ include, but are not limited to, structures derivable from nonconjugated terminal diolefins, such as —CH(CH$_2$—) (CH$_2$)$_q$CH(CH$_2$—)—, in which q is from 1 to 20; any of the structures derivable from divinylbenzene, such as —CH$_2$(CH—)(C$_6$H$_4$)CH(CH$_2$—)—, where the notation C$_6$H$_4$ denotes a disubstituted benzene ring; any of the structures derivable from diallylether, such as —CH$_2$(CH—)CH$_2$OCH$_2$CH(CH$_2$—)—; any of the structures derivable from butadiene, such as —CH$_2$(CH—)(CH—)CH$_2$—; any of the structures derivable from piperylene, such as —CH$_2$(CH—) (CH—)CH$_2$(CH$_3$)—; any of the structures derivable from isoprene, such as —CH$_2$(C—) (CH$_3$)(CH—)CH$_2$—; any of the vinyl-containing structures derivable from trivinylcyclohexane, such as —CH$_2$(CH—)(vinylC$_6$H$_9$)(CH—)CH$_2$—, —CH$_2$CH$_2$C$_6$H$_9$[(CH—)CH$_2$—]$_2$, —CH(CH$_3$)C$_6$H$_9$[(CH—)CH$_2$—]$_2$, and C$_6$H$_9$[(CH—)CH$_2$—]$_3$, where the notation C$_6$H$_9$ denotes any isomer of the trisubstituted cyclohexane ring; any of the saturated structures derivable from trivinylcyclohexane, such as —CH$_2$(CH—)C$_6$H$_9$[CH$_2$CH$_2$—]$_2$, and —CH$_2$(CH—)C$_6$H$_9$[CH(CH$_3$)—][CH$_2$CH$_2$—], where the notation C$_6$H$_9$ denotes any isomer of the trisubstituted cyclohexane ring; any of the monounsaturated structures derivable from myrcene containing a trisubstituted C=C, such as —CH$_2$(C—)[CH$_2$CH$_2$CH=C(CH$_3$)$_2$]CH$_2$CH$_2$—, —CH$_2$CH[CH$_2$CH$_2$CH=C(CH$_3$)$_2$](CH—)CH$_2$—; and pentaerythrityl, whose structure is C(CH$_2$—)$_4$.

Representative examples of didentate $G^2$ include, but are not limited to, structures derivable from nonconjugated terminal diolefins, such as —CH$_2$(CH$_2$)$_{q+1}$CH$_2$(CH$_2$—) and CH$_2$(CH$_3$)(CH$_2$)$_q$CH(CH$_2$—)$_2$, in which q is zero to 20; any of the structures derivable from divinylbenzene, such as —CH$_2$CH$_2$(C$_6$H$_4$)CH$_2$CH$_2$—, where the notation C$_6$H$_4$ denotes a disubstituted benzene ring; any of the structures derivable from butadiene, such as —CH$_2$CH$_2$CH$_2$CH$_2$—; any of the structures derivable from isoprene, such as —CH$_2$(CH)(CH$_3$)CH$_2$CH$_2$—, and —CH$_2$CH(CH$_3$)CH$_2$CH$_2$—; any structures derivable from trivinylcyclohexane, such as —CH$_2$CH$_2$(vinylC$_6$H$_9$)CH$_2$CH$_2$—, and (—CH$_2$CH$_2$)C$_6$H$_9$CH$_2$CH$_3$, where the notation C$_6$H$_9$ denotes any isomer of the trisubstituted cyclohexane ring; any of the structures derivable from myrcene, such as, —CH$_2$(CH)[CH$_2$CH$_2$CH=C(CH$_3$)$_2$]CH$_2$CH$_2$—; and the diethanolamine derivative, (—CH$_2$CH$_2$)NCH$_3$.

Representative examples of tridentate $G^2$ include, but are not limited to, structures derivable from nonconjugated terminal diolefins, such as —CH$_2$(CH$_2$)$_{q+1}$CH(CH$_2$—)— in which q is zero to 20; structures derivable from trivinylcyclohexane, such as (—CH$_2$CH$_2$)$_3$C$_6$H$_9$, where the notation C$_6$H$_9$ denotes any isomer of the trisubstituted cyclohexane ring; the structures derivable from trimethylolalkanes, such as CH$_3$CH$_2$CH$_2$C(CH$_2$—)$_3$ and CH$_3$CH$_2$C(CH$_2$—)$_3$; and the triethanolamine derivative, (—CH$_2$CH$_2$)$_3$N.

Representative examples of silated core polysulfide silanes of the present invention include any of the isomers of 2-triethoxysilyl-1,3-bis-(3-triethoxysilyl-1-propyltetrathia)propane; 4-(2-triethoxysilyl-1-ethyl)-1,2-bis-(1,3-triethoxysilyl-3,4,5,6-tetrathiatridecyl)cyclohexane; 4-(2-triethoxysilyl-1-ethyl)-1,2-bis-(1,3-triethoxysilyl-3,4,5,6-tetrathiatridecyl)cyclohexane; 4-(2-diethoxymethylsilyl-1-ethyl)-1,2-bis-(13-triethoxysilyl-3,4,5,6-tetrathiatridecyl)cyclohexane; 4-(2-triethoxysilyl-1-ethyl)-1,2-bis-(10-triethoxysilyl-3,4,5,6,7-pentathiadecyl)cyclohexane; 1-(2-triethoxysilyl-1-ethyl)-2,4-bis-(10-triethoxysilyl-3,4,5,6,7-pentathiadecyl)cyclohexane; 4-(2-triethoxysilyl-1-ethyl)-1,2-bis-(9-triethoxysilyl-3,4,5,6-tetrathianonyl)cyclohexane; 1-(2-triethoxysilyl-1-ethyl)-2,4-bis-(9-triethoxysilyl-3,4,5,6-tetrathianonyl)cyclohexane; 2-(2-triethoxysilyl-1-ethyl)-1,4-bis-(9-triethoxysilyl-3,4,5,6-tetrathianonyl)cyclohexane; 4-(2-triethoxysilyl-1-ethyl)-1,2-bis-(8-triethoxysilyl-3,4,5-trithiaoctyl)cyclohexane; 1-(2-triethoxysilyl-1-ethyl)-2,4-bis-(8-triethoxysilyl-3,4,5-trithiaoctyl)cyclohexane; 2-(2-triethoxysilyl-1-ethyl)-1,4-bis-(8-triethoxysilyl-3,4,5-trithiaoctyl)cyclohexane; 4-(2-triethoxysilyl-1-ethyl)-1,2-bis-(7-triethoxysilyl-3,4-dithiaheptyl)cyclohexane; 2-(2-triethoxysilyl-1-ethyl)-1,4-bis-(7-triethoxysilyl-3,4-dithiaheptyl)cyclohexane; 1-(2-triethoxysilyl-1-ethyl)-2,4-bis-(7-triethoxysilyl-3,4-dithiaheptyl)cyclohexane; 2-(2-triethoxysilyl-1-ethyl)-1-(7-triethoxysilyl-3,4-dithiaheptyl)-2-(8-triethoxysilyl-3,4,5-trithiaoctyl)cyclohexane; 4-(2-triethoxysilyl-1-ethyl)-1,2-bis-(9-triethoxysilyl-3,4,5,6-tetrathianonyl)benzene; bis-[2-[4-(2-triethoxysilyl-1-ethyl)-2-(9-triethoxysilyl-3,4,5,6-tetrathianonyl)cyclohexyl]ethyl]tetrasulfide; bis-[2-[4-(2-triethoxysilyl-1-ethyl)-2-(9-triethoxysilyl-3,4,5,6-tetrathianonyl)cyclohexyl]ethyl]trisulfide; bis-[2-[4-(2-triethoxysilyl-1-ethyl)-2-(9-triethoxysilyl-3,4,5,6-tetrathianonyl)cyclohexyl]ethyl]disulfide; bis-[2-[4-(2-triethoxysilyl-1-ethyl)-2-(7-triethoxysilyl-3,4-dithiaheptyl)cyclohexyl]ethyl]disulfide; bis-2-[4-(2-triethoxysilyl-1-ethyl)-2-(7-triethoxysilyl-3,4-dithiaheptyl)cyclohexyl]ethyl]trisulfide; bis-[2-[4-(2-triethoxysilyl-1-ethyl)-2-(7-triethoxysilyl-3,4-dithiaheptyl)cyclohexyl]ethyl tetrasulfide; bis-[2-[4-(2-triethoxysilyl-1-ethyl)-2-(9-triethoxysilyl-3,4,5,6-tetrathianonyl)phenyl]ethyl]tetrasulfide; bis-2-[4-(2-triethoxysilyl-1-ethyl)-3-bis-(9-triethoxysilyl-3,4,5,6-tetrathianonyl)cyclohexyl]ethyl] trisulfide; bis-[2-[4-(2-diiethoxymethylsilyl-1-ethyl)-2-(7-triethoxysilyl-3,4-dithiaheptyl)cyclohexyl]ethyl disulfide.

A another embodiment of the present invention the Formulae (1), (2) and (3), are described wherein each occurrence of $R^1$ and $R^3$ are independently selected from a divalent hydrocarbon fragment having from 1 to about 5 carbon atoms that include branched and straight chain alkyl, alkenyl, alkynyl, aryl or aralkyl groups in which one hydrogen atom was substituted with a $Y^1$ or $Y^2$ group; each occurrence of $Y^1$ and $Y^2$ is chosen independently from silyl (—$SiX^1,X^2,X^3$); each occurrence of $R^2$ is a straight chain hydrocarbon represented by —$(CH_2)_f$— where f is an integer from about 0 to about 3; each occurrence of $R^4$ is chosen independently from a polyvalent hydrocarbon fragment of 3 to about 10 carbon atom that was obtained by substitution of hydrogen atoms equal to the sum of a+c+e, and include cyclic alkyl or aryl in which a+c+e–1 hydrogens have been replaced; each occurrence of $R^5$ is chosen independently from a polyvalent hydrocarbon fragment of 3 to about 10 carbon atom that was obtained by substitution of hydrogen atoms equal to the sum of c+e, and include branched and straight chain alkyl, alkenyl, alkynyl, aryl and aralkyl groups in which c+e–1 hydrogens have been replaced; each occurrence of $X^1$ is chosen independently from the set of hydrolyzable groups consisting of —OH, and —$OR^6$, in which $R^6$ is any monovalent hydrocarbon group having from 1 to 5 carbon atoms, and includes branched or straight chain alkyl, alkenyl, aryl or aralkyl groups; each occurrence of $X^2$ and $X^3$ is chosen independently taken from the group consisting of the members listed above for $R^6$, the members listed above for $X^1$ and —OSi containing groups that result from the condensation of silanols; each occurrence of the subscripts, a, b, c, d, e, f, m, n, o, p, and x, is independently given by a is 1 to about 2; b is 1 to about 3; c is 1; d is 1 to about 3; e is 1; f is 0 to about 3; m is 1, n is 1 to about 10; o is 0 to about 1; p is 1, and x is 1 to about 4.

In another embodiment, 30 to 99 weight percent of the silated core polysulfide of the present invention is blended with 70 to 1 weight percent of another silane, including silanes of the structure represented in Formula (4)

$$[X^1X^2X^3SiR^1S_xR^3SiX^1X^2X^3] \qquad \text{(Formula 4)}$$

Representative examples of the silanes described by Formula 4 are listed in U.S. Pat. No. 3,842,111, which is incorporated herein by reference, and include bis-(3-triethoxysilylpropyl) disulfide; bis-(3-triethoxysilylpropyl)trisulfide; bis-(3-triethoxysilylpropyl)tetrasulfide; bis-(3-triethoxysilylpropyl) pentasulfide; bis-(3-diethoxymethylsilylpropyl) disulfide; bis-(3-ethoxydimethylsilylpropyl) disulfide; bis-(triethoxysilylmethyl) disulfide; bis-(4-triethoxysilylbenzyl) disulfide; bis-(3-triethoxysilylphenyl) disulfide and the like.

The bonding of sulfur to a methylene group on $R^4$ and $R^5$ is required because the methylene group mitigates excessive steric interactions between the silane and the filler and polymer. Two successive methylene groups mitigate steric interactions even further and also add flexibility to the chemical structure of the silane, thereby enhancing its ability to accommodate the positional and orientational constraints imposed by the morphologies of the surfaces of both the rubber and filler at the interphase, at the molecular level. The silane flexibility becomes increasingly important as the total number of silicon and sulfur atoms bound to $G^1$ and $G^2$ increases from 3 to 4 and beyond. Structures in which the polysulfide group is bonded directly to secondary and tertiary carbon atoms, ring structures, especially aromatic structures, are rigid and sterically hindered. The accelerators and curatives cannot readily orient themselves with the polysulfide group to affect reaction and the silated core polysulfide cannot readily orient itself to meet available binding sites on silica and polymer. This would tend to leave sulfur groups unbound to polymer, thereby reducing the efficiency by which the principle of multiple bonding of silane to polymer via multiple sulfur groups on silane, is realized.

The function of the other silanes in the blend is to occupy sites on the surface of the silica which aid in dispersing the silica and coupling with the polymer.

Process for Preparing Silated Core Polysulfides

In another embodiment of the present invention, the silated core polysulfides are prepared by (a) reacting a hydrosilane of the structure, $HSi(X^1X^2X^3)$, with a hydrocarbon containing reactive double bonds; (b) reacting the intermediate product from step (a) with a sulfuring agent, selected from the group $R^6C(=O)SH$, where $R^6$ is as previously defined, in the presence of a free radical agent; (c) deblocking the mercapto group using a proton donator; (d) reacting the intermediate mercaptan in step c with a mixture of base and sulfur; and (e) reacting the intermediate in step d with a substituted or unsubstituted hydrocarbon containing a leaving group selected from chlorine, bromine or iodine.

The structure of the hydrocarbon containing reactive double bonds in step (a) can be represented by the chemical structure shown if Formula (5)

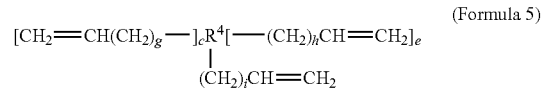
$$[CH_2\!=\!CH(CH_2)_g\!-\!]_cR^4[\!-\!(CH_2)_h CH\!=\!CH_2]_e \qquad \text{(Formula 5)}$$
$$|$$
$$(CH_2)_i CH\!=\!CH_2$$

wherein each occurrence is described supra and the subscripts g, h and i are independently given by g is about 0 to 3; h is 0 to about 3; and i is 0 to about 3.

The free radical reagent includes oxidizing agents that are capable of converting the thiocarboxylic acid to a thiocarboxylic acid radical, i.e. $R^6C(=O)S\cdot$, and include, but are not limited to oxygen, peroxides, hydroperoxides, and the like.

The proton donor species are any hydrogen containing heterocarbon or substituted heterocarbon that is capable of reacting with the thiocarboxylic acid ester intermediate in step (c) to generate an unblocked mercaptan. Representative examples of these hydrogen donor species include, but are not limited to, alcohols, such as methanol, ethanol, isopropyl alcohol, propanol, and the like; amines such as ammonia, methyl amine, propyl amine, diethanol amine, and the like; mercaptans, such as propyl mercaptans, butyl mercaptan, and the like.

The structure of the substituted or unsubstituted hydrocarbon containing a leaving group is represented by Formulae (6) and (7)

$$Y^1R^1Z \qquad \text{(Formula 6)}$$

$$Y^2R^3Z \qquad \text{(Formula 7)}$$

wherein each occurrence of $Y^1$, $Y^2$, $R^1$, and $R^2$ are as previously defined and Z is selected from the group Cl, Br and I.

The reactions may be carried out in the presence or absence of organic solvents, including alcohols, ethers, hydrocarbon solvents, and the like. Representative examples of suitable organic solvents include, but are not limited to, ethanol, methanol, isopropyl alcohol, tetrahydrofuran, diethyl ether, hexanes, cyclohexane, toluene, xylenes, and mixtures thereof, and the like.

Use in Rubber Compositions

In one embodiment of the present invention, a rubber composition comprising:
(a) a rubber;
(b) the silated core polysulfide of the present invention (Formula 1);
(c) a filler.

In another embodiment of the present invention, a cured rubber composition comprising:
(a) a rubber;
(b) a silated core polysulfide of the present invention (Formula 1);
(c) a filler;
(d) curatives; and
(e) optionally, other additives.

The rubbers useful with the coupling agents described herein include sulfur vulcanizable rubbers including conjugated diene homopolymers and copolymers, and copolymers of at least one conjugated diene and aromatic vinyl compound. Suitable organic polymers for preparation of rubber compositions are well known in the art and are described in various textbooks including *The Vanderbilt Rubber Handbook*, Ohm, R. F., R. T. Vanderbilt Company, Inc., 1990 and in the *Manual for the Rubber Industry*, Kemperman, T. and Koch, S. Jr., Bayer A G, LeverKusen, 1993.

One example of a suitable polymer for use herein is solution-prepared styrene-butadiene rubber (SSBR). This solution prepared SSBR typically has a bound styrene content in a range of 5 to 50, preferably 9 to 36, percent. Other useful polymers include emulsion-prepared styrene-butadiene rubber (ESBR), natural rubber (NR), ethylene-propylene copolymers and terpolymers (EP, EPDM), acrylonitrile-butadiene rubber (NBR), polybutadiene (BR), and so forth.

In another embodiment, the rubber composition is comprised of at least one diene-based elastomer, or rubber. Suitable conjugated dienes include, but are not limited to, isoprene and 1,3-butadiene and suitable vinyl aromatic compounds include, but are not limited to, styrene and alpha methyl styrene. Polybutadiene may be characterized as existing primarily, typically about 90% by weight, in the cis-1,4-butadiene form, but other compositions may also be used for the purposes described herein.

Thus, the rubber is a sulfur curable rubber. Such diene based elastomer, or rubber, may be selected, for example, from at least one of cis-1,4-polyisoprene rubber (natural and/or synthetic), emulsion polymerization prepared styrene/butadiene copolymer rubber, organic solution polymerization prepared styrene/butadiene rubber, 3,4-polyisoprene rubber, isoprene/butadiene rubber, styrene/isoprene/butadiene terpolymer rubber, cis-1,4-polybutadiene, medium vinyl polybutadiene rubber (35-50 percent vinyl), high vinyl polybutadiene rubber (50-75 percent vinyl), styrene/isoprene copolymers, emulsion polymerization prepared styrene/butadiene/acrylonitrile terpolymer rubber and butadiene/acrylonitrile copolymer rubber. For some applications, an emulsion polymerization derived styrene/butadiene (ESBR) having a relatively conventional styrene content of about 20 to 28 percent bound styrene, or an ESBR having a medium to relatively high bound styrene content of about 30 to 45 percent may be used.

Emulsion polymerization prepared styrene/butadiene/acrylonitrile terpolymer rubbers containing 2 to 40 weight percent bound acrylonitrile in the terpolymer are also contemplated as diene based rubbers for use in this invention.

A particulate filler may also be added to the crosslinkable elastomer compositions of the present invention including siliceous fillers, carbon black, and so forth. The filler materials useful herein include, but are not limited to, metal oxides such as silica (pyrogenic and/or precipitated), titanium dioxide, aluminosilicate and alumina, clays and talc, carbon black, and so forth.

Particulate, precipitated silica is also sometimes used for such purpose, particularly when the silica is used in conjunction with a silane. In some cases, a combination of silica and carbon black is utilized for reinforcing fillers for various rubber products, including treads for tires. Alumina can be used either alone or in combination with silica. The term, alumina, can be described herein as aluminum oxide, or $Al_2O_3$. The fillers may be hydrated or in anhydrous form.

The silated core polysulfide silane(s) may be premixed or pre-reacted with the filler particles, or added to the rubber mix during the rubber and filler processing, or mixing stages. If the silated core polysulfide silanes and filler are added separately to the rubber mix during the rubber and filler mixing, or processing stage, it is considered that the silated core polysulfide silane(s) then combine(s) in an in-situ fashion with the filler.

The vulcanized rubber composition should contain a sufficient amount of filler to contribute a reasonably high modulus and high resistance to tear. In one embodiment of the present invention, the combined weight of the filler may be as low as about 5 to about 100 parts per hundred parts rubber (phr). In another embodiment, the combined weight of the filler is from about 25 to about 85 phr and at least one precipitated silica is utilized as a filler. The silica may be characterized by having a BET surface area, as measured using nitrogen gas, in the range of about 40 to about 600 $m^2/g$. In another embodiment of the invention, the silica has a BET surface area in a range of about 50 to about 300 $m^2/g$. The BET method of measuring surface area is described in the *Journal of the American Chemical Society*, Volume 60, page 304 (1930). The silica typically may also be characterized by having a dibutylphthalate (DBP) absorption value in a range of about 100 to about 350, and more usually about 150 to about 300. Further, the silica, as well as the aforesaid alumina and aluminosilicate, may be expected to have a CTAB surface area in a range of about 100 to about 220. The CTAB surface area is the external surface area as evaluated by cetyl trimethylammonium bromide with a pH of about 9. The method is described in ASTM D 3849.

Mercury porosity surface area is the specific surface area determined by mercury porosimetry. Using this method, mercury is penetrated into the pores of the sample after a thermal treatment to remove volatiles. Set up conditions may be suitably described as using about a 100 mg sample; removing volatiles during about 2 hours at about 105° C. and ambient atmospheric pressure; ambient to about 2000 bars pressure measuring range. Such evaluation may be performed according to the method described in Winslow, Shapiro in ASTM bulletin, p. 39 (1959) or according to DIN 66133. For such an evaluation, a CARLO-ERBA Porosimeter 2000 might be used. The average mercury porosity specific surface area for the silica should be in a range of about 100 to about 300 $m^2/g$.

In one embodiment, a suitable pore size distribution for the silica, alumina and aluminosilicate according to such mercury porosity evaluation is considered herein to be such that five percent or less of its pores have a diameter of less than about 10 nm, about 60 to about 90 percent of its pores have a diameter of about 10 to about 100 nm, about 10 to about 30 percent of its pores have a diameter at about 100 to about 1,000 nm, and about 5 to about 20 percent of its pores have a diameter of greater than about 1,000 nm.

In a second embodiment the silica might be expected to have an average ultimate particle size, for example, in the range of about 10 to about 50 nm as determined by the electron microscope, although the silica particles may be even smaller, or possibly larger, in size. Various commercially available silicas may be considered for use in this invention such as, from PPG Industries under the HI-SIL trademark with designations HI-SIL 210, 243, etc.; silicas available from Rhone-Poulenc, with, for example, designation of ZEOSIL 1165 MP; silicas available from Degussa with, for example, designations VN2 and VN3, etc. and silicas commercially available from Huber having, for example, a designation of HUBERSIL7 8745.

In still another embodiment of the invention, the compositions may utilize siliceous fillers such as silica, alumina and/or aluminosilicates in combination with carbon black reinforcing pigments. The compositions may comprise a filler mix of about 15 to about 95 weight percent of the siliceous filler, and about 5 to about 85 weight percent carbon black, wherein the carbon black has a CTAB value in a range of about 80 to about 150. More typically, it is desirable to use a weight ratio of siliceous fillers to carbon black of at least about 3/1 in one embodiment, and at least about 10/1 in another embodiment. Thus, the weight ratio may range from about 3/1 to about 30/1 for siliceous fillers to carbon black.

In another embodiment of the invention, the filler can be comprised of about 60 to about 95 weight percent of said silica, alumina and/or aluminosilicate and, correspondingly, about 40 to about 5 weight percent carbon black. The siliceous filler and carbon black may be pre-blended or blended together in the manufacture of the vulcanized rubber.

In yet another embodiment of the present invention, the rubber compositions of the present invention are prepared by mixing one or more of the silated core polysulfide silanes with the organic polymer before, during or after the compounding of the filler into the organic polymer. In another embodiment, the silated core polysulfide silanes are added before or during the compounding of the filler into the organic polymer, because these silanes facilitate and improve the dispersion of the filler. In another embodiment, the total amount of silated core polysulfide silane present in the resulting combination should be about 0.05 to about 25 parts by weight per hundred parts by weight of organic polymer (phr); and 1 to 10 phr in another embodiment. In yet another embodiment, fillers can be used in quantities ranging from about 5 to about 120 phr, and still in another embodiment, fillers can be used in quantities ranging from about 25 to about 110 phr, or about 25 to about 105 phr.

In practice, sulfur vulcanized rubber products typically are prepared by thermomechanically mixing rubber and various ingredients in a sequentially step-wise manner followed by shaping and curing the compounded rubber to form a vulcanized product. First, for the aforesaid mixing of the rubber and various ingredients, typically exclusive of sulfur and sulfur vulcanization accelerators (collectively, curing agents), the rubber(s) and various rubber compounding ingredients typically are blended in at least one, and often (in the case of silica filled low rolling resistance tires) two or more, preparatory thermomechanical mixing stage(s) in suitable mixers. Such preparatory mixing is referred to as nonproductive mixing or non-productive mixing steps or stages. Such preparatory mixing usually is conducted at temperatures of about 140° C. to about 200° C., and for some compositions, about 150° C. to about 180° C. Subsequent to such preparatory mix stages, in a final mixing stage, sometimes referred to as a productive mix stage, curing agents, and possibly one or more additional ingredients, are mixed with the rubber compound or composition, at lower temperatures of typically about 50° C. to about 130° C. in order to prevent or retard premature curing of the sulfur curable rubber, sometimes referred to as scorching. The rubber mixture, also referred to as a rubber compound or composition, typically is allowed to cool, sometimes after or during a process intermediate mill mixing, between the aforesaid various mixing steps, for example, to a temperature of about 50° C. or lower. When it is desired to mold and to cure the rubber, the rubber is placed into the appropriate mold at a temperature of at least about 130° C. and up to about 200° C. which will cause the vulcanization of the rubber by the S—S bond-containing groups (i.e., disulfide, trisulfide, tetrasulfide, etc.; polysulfide) on the silated core polysulfide silanes and any other free sulfur sources in the rubber mixture.

Thermomechanical mixing refers to the phenomenon whereby under the high shear conditions in a rubber mixer, the shear forces and associated friction occurring as a result of mixing the rubber compound, or some blend of the rubber compound itself and rubber compounding ingredients in the high shear mixer, the temperature autogeneously increases, i.e. it "heats up". Several chemical reactions may occur at various steps in the mixing and curing processes.

The first reaction is a relatively fast reaction and is considered herein to take place between the filler and the silicon alkoxide group of the silated core polysulfides. Such reaction may occur at a relatively low temperature such as, for example, at about 120° C. The second reaction is considered herein to be the reaction which takes place between the sulfur-containing portion of the silated core polysulfide silane, and the sulfur vulcanizable rubber at a higher temperature; for example, above about 140° C.

Another sulfur source may be used, for example, in the form of elemental sulfur, such as but not limited to $S_8$. A sulfur donor is considered herein as a sulfur containing compound which liberates free, or elemental sulfur, at a temperature in a range of about 140° C. to about 190° C. Such sulfur donors may be, for example, although are not limited to, polysulfide vulcanization accelerators and organosilane polysulfides with at least two connecting sulfur atoms in its polysulfide bridge. The amount of free sulfur source addition to the mixture can be controlled or manipulated as a matter of choice relatively independently from the addition of the aforesaid silated core polysulfide silane. Thus, for example, the independent addition of a sulfur source may be manipulated by the amount of addition thereof and by the sequence of addition relative to the addition of other ingredients to the rubber mixture.

In one embodiment of the invention, the rubber composition may therefore comprise about 100 parts by weight of at least one sulfur vulcanizable rubber selected from the group consisting of conjugated diene homopolymers and copolymers, and copolymers of at least one conjugated diene and aromatic vinyl compound, about 5 to 100 parts, preferably about 25 to 80 parts per hundred parts by weight per 100 parts by weight rubber of at least one particulate filler, up to about 5 parts by weight per 100 parts by weight rubber of a curing agent, and about 0.05 to about 25 parts per hundred parts of polymer of at least one silated core polysulfide silane as described in the present invention.

In another embodiment of the present invention, the filler comprises from about 1 to about 85 weight percent carbon black based on the total weight of the filler and 0 to about 20 parts by weight of at least one silated core polysulfide silane based on the total weight of the filler.

In still another embodiment, the rubber composition is prepared by first blending rubber, filler and silated core polysulfide silane, or rubber, filler pretreated with all or a portion of the silated core polysulfide silane and any remaining silated core polysulfide silane, in a first thermomechanical mixing step to a temperature of about 140° C. to about 200° C. for about 2 to about 20 minutes. In another embodiment, filler pretreated with all or a portion of the silated core polysulfide silane and any remaining silated core polysulfide silane, in a first thermomechanical mixing step to a temperature of about 140° C. to about 200° C. for about 4 to 15 minutes. Optionally, the curing agent is then added in another thermomechanical mixing step at a temperature of about 50° C. and mixed for about 1 to about 30 minutes. The temperature is then heated again to between about 130° C. and about 200° C. and curing is accomplished in about 5 to about 60 minutes.

In another embodiment of the present invention, the process may also comprise the additional steps of preparing an assembly of a tire or sulfur vulcanizable rubber with a tread comprised of the rubber composition prepared according to this invention and vulcanizing the assembly at a temperature in a range of about 130° C. to about 200° C.

Other optional ingredients may be added in the rubber compositions of the present invention including curing aids, i.e. sulfur compounds, activators, retarders and accelerators, processing additives such as oils, plasticizers, tackifying resins, silicas, other fillers, pigments, fatty acids, zinc oxide, waxes, antioxidants and antiozonants, peptizing agents, reinforcing materials such as, for example, carbon black, and so forth. Such additives are selected based upon the intended use and on the sulfur vulcanizable material selected for use, and such selection is within the knowledge of one of skill in the art, as are the required amounts of such additives known to one of skill in the art.

The vulcanization may be conducted in the presence of additional sulfur vulcanizing agents. Examples of suitable sulfur vulcanizing agents include, for example elemental sulfur (free sulfur) or sulfur donating vulcanizing agents, for example, an amino disulfide, polymeric polysulfide or sulfur olefin adducts which are conventionally added in the final, productive, rubber composition mixing step. The sulfur vulcanizing agents, which are common in the art are used, or added in the productive mixing stage, in an amount ranging from about 0.4 to about 3 phr, or even, in some circumstances, up to about 8 phr, with a range of from about 1.5 to about 2.5 phr and all subranges therebetween in one embodiment from 2 to about 2.5 phr and all subranges therebetween in another embodiment.

Optionally, vulcanization accelerators, i.e., additional sulfur donors, may be used herein. It is appreciated that may include the following examples, benzothiazole, alkyl thiuram disulfide, guanidine derivatives and thiocarbamates. Representative of such accelerators can be, but not limited to, mercapto benzothiazole (MBT), tetramethyl thiuram disulfide (TMTD), tetramethyl thiuram monosulfide (TMTM), benzothiazole disulfide (MBTS), diphenylguanidine (DPG), zinc dithiocarbamate (ZBEC), alkylphenoldisulfide, zinc isopropyl xanthate (ZIX), N-dicyclohexyl-2-benzothiazole-sulfenamide (DCBS), N-cyclohexyl-2-benzothiazolesulfenamide (CBS), N-tert-buyl-2-benzothiazolesulfenamide (TBBS), N-tert-buyl-2-benzothiazolesulfenimide (TBSI), tetrabenzylthiuram disulfide (TBzTD), tetraethylthiuram disulfide (TETD), N-oxydiethylenebenzothiazole-2-sulfenamide, N,N-diphenylthiourea, dithiocarbamylsulfenamide, N,N-diisopropylbenzothiozole-2-sulfenamide, zinc-2-mercaptotoluimidazole, dithiobis(N-methyl piperazine), dithiobis(N-beta-hydroxy ethyl piperazine) and dithiobis(dibenzyl amine). Other additional sulfur donors, may be, for example, thiuram and morpholine derivatives. Representative of such donors are, for example, but not limited to, dimorpholine disulfide, dimorpholine tetrasulfide, tetramethyl thiuram tetrasulfide, benzothiazyl-2,N-dithiomorpholide, thioplasts, dipentamethylenethiuram hexasulfide, and disulfidecaprolactam.

Accelerators are used to control the time and/or temperature required for vulcanization and to improve the properties of the vulcanizate. In one embodiment, a single accelerator system may be used, i.e., a primary accelerator. Conventionally, a primary accelerator(s) is used in total amounts ranging from about 0.5 to about 4 phr and all subranges therebetween in one embodiment, and from about 0.8 to about 1.5, phr and all subranges therebetween in another embodiment. Combinations of a primary and a secondary accelerator might be used with the secondary accelerator being used in smaller amounts (of about 0.05 to about 3 phr and all subranges therebetween) in order to activate and to improve the properties of the vulcanizate. Delayed action accelerators may be used. Vulcanization retarders might also be used. Suitable types of accelerators are amines, disulfides, guanidines, thioureas, thiazoles, thiurams, sulfenamides, dithiocarbamates and xanthates. In one embodiment, the primary accelerator is a sulfenamide. If a second accelerator is used, the secondary accelerator can be a guanidine, dithiocarbamate and/or thiuram compounds. Preferably, tetrabenzylthiuram disulfide is utilized as a secondary accelerator in combination with N-tert-buyl-2-benzothiazolesulfenamide with or without diphenylguanidine. Tetrabenzylthiuram disulfide is a preferred accelerator as it does not lead to the production of nitrosating agents, such as, for example, tetramethylthiuram disulfide.

Typical amounts of tackifier resins, if used, comprise about 0.5 to about 10 phr and all subranges therebetween, usually about 1 to about 5 phr and all subranges therebetween. Typical amounts of processing aids comprise about 1 to about 50 phr and all subranges therebetween. Such processing aids can include, for example, aromatic, napthenic, and/or paraffinic processing oils. Typical amounts of antioxidants comprise about 1 to about 5 phr. Representative antioxidants may be, for example, diphenyl-p-phenylenediamine and others, such as, for example, those disclosed in the *Vanderbilt Rubber Handbook* (1978), pages 344-346. Typical amounts of antiozonants, comprise about 1 to about 5 phr and all subranges therebetween. Typical amounts of fatty acids, if used, which can include stearic acid, comprise about 0.5 to about 3 phr and all subranges therebetween. Typical amounts of zinc oxide comprise about 2 to about 5 phr. Typical amounts of waxes comprise about 1 to about 5 phr and all subranges therebetween. Often microcrystalline waxes are used. Typical amounts of peptizers comprise about 0.1 to about 1 phr and all subranges therebetween. Typical peptizers may be, for example, pentachlorothiophenol and dibenzamidodiphenyl disulfide.

The rubber compositions of this invention can be used for various purposes. For example, it can be used for various tire compounds, weather stripping, and shoe soles. In one embodiment of the present invention, the rubber compositions described herein are particularly useful in tire treads, but may also be used for all other parts of the tire as well. The tires can be built, shaped, molded and cured by various methods which are known and will be readily apparent to those having skill in such art.

In another embodiment, the silated core polysulfide of the present invention compositions may be loaded on a carrier, or filler, such as, for example, a porous polymer, carbon black, silica or the like, so that they are in a dry free flowing form for convenient delivery to rubber. In one embodiment, the carrier would be part of the inorganic filler to be used in the rubber.

In one embodiment of the invention, a dry free flowing composition comprises a silane in accordance with this invention in admixture with one or more of the aforesaid carrier materials, e.g., in a weight ratio of from about 0.1 to about 60 weight percent. The BET surface area of such carriers as silica can vary widely and in one embodiment can vary from about 100 m²/g to about 300 m²/g. Another property of such carriers is their DOP adsorption, an oil adsorption index. In the case of nonporous carriers such as silica, the DOP adsorption can range from about 100 ml/100 gm to about 400 ml/100 gm. Porous carriers such as foamed polyolefins can advantageously absorb from about 10 ml to about 250 ml/100 gm (from about 9 to about 70 weight percent) of the silane of the present invention.

The filler can be essentially inert to the silane with which it is admixed as is the case with carbon black or organic polymers, or it can be reactive therewith, e.g., the case with carriers possessing metal hydroxyl surface functionality, e.g., silicas and other siliceous particulates which possess surface silanol functionality.

EXAMPLES

The examples presented below demonstrate significant advantages of the silanes described herein relative those of the currently practiced art, in their performance as coupling agents in silica-filled rubber.

Example 1

Preparation of (2-triethoxysilylethyl)-bis-(7-triethoxysilyl-3,4-dithiaheptyl)cyclohexane This example illustrates the preparation of a silated core disulide from a silane containing two vinyl groups through the formation of an intermediate thioacetate silane. The preparation of the (2-trimethoxysilylethyl)divinylcyclohexane was prepared by hydrosilation. Into a 5 L, three-neck round bottomed flask equipped with magnetic stir bar, temperature probe/controller, heating mantle, addition funnel, condenser, and air inlet were charged 1,2,4-trivinylcyclohexane (2,001.1 grams, 12.3 moles) and VCAT catalysts (1.96 grams, 0.01534 gram platinum). Air was bubbled into the vinyl silane by means of the air inlet where the tube was below the surface of the silane. The reaction mixture was heated to 110° C. and the trimethoxysilane (1,204 grams, 9.9 moles) was added over a 3.5 hour period. The temperature of the reaction mixture increased to a maximum value of 130° C. The reaction mixture was cooled to room temperature and 1,3,5-trimethyl-2,4,6-tris(3,5-di-tert-butyl-4-hydroxylbenzyl)benzene (3 grams, 0.004 mole) was added. The reaction mixture was distilled at 122° C. and 1 mmHg pressure to give 1,427 grams of (2-trimethoxysilylethyl)divinylcyclohexane, The yield was 51 percent.

The (2-triethoxysilylethyl)divinylcyclohexane was prepared by transesterification. Into a 3 L, three-neck round bottomed flask equipped with magnetic stir bar, temperature probe/controller, heating mantle, addition funnel, distilling head and condenser, and nitrogen inlet were charged (2-trimethoxysilylethyl)divinylcyclohexane (284 grams, 2.33 moles), sodium ethoxide in ethanol (49 grams of 21% sodium ethoxide, purchased from Aldrich Chemical) and ethanol (777 grams, 16.9 moles). The reaction mixture was heated and the methanol and ethanol were removed by distillation at atmospheric pressure. The crude product was then distilled at 106° C. and under reduced pressure of 0.4 mmHg to give 675 grams of product, 89 percent yield.

The (2-triethoxysilylethyl)-bis-(3-thia-4-oxopentyl)cyclohexane was prepared by addition of thioacetic acid to the divinylsilane. Into a 1 L, three-neck round bottomed flask equipped with magnetic stir bar, temperature probe/controller, heating mantle, addition funnel, condenser, air inlet and a sodium hydroxide scrubber, was charged thioacetic acid (210 grams, 2.71 moles). The (2-triethoxysilylethyl)divinylcyclohexane (400 grams, 1.23 moles) was added slowly over a period of 30 minutes and at room temperature by means of an addition funnel. The reaction was an exothermic reaction. The temperature of the mixture increased to 94.6° C. The mixture was stirred for 2.5 hours and allowed to cool to 38.8° C. Additional thioacetic acid (10 grams, 0.13 moles) was added and a slight exothermal reaction was observed. The reaction mixture was stirred overnight (18 hours) at about 25° C. Analysis indicated that the reaction mixture contained less than 2 percent thioacetic acid. Its overall purity was 91 percent. The reaction mixture was further purified by a distillation using a Kugel apparatus under reduced pressure.

The dimercaptosilane intermediate was prepared by removing the acetyl groups from (2-triethoxysilylethyl)-bis-(3-thia-4-oxopentyl)cyclohexane. Into a 5 L, three-neck round bottomed flask equipped with magnetic stir bar, temperature probe/controller, heating mantle, addition funnel, distilling head and condenser, 10-plate Oldershaw column and nitrogen inlet were charged (2-triethoxysilylethyl)bis-(3-thia-4-oxopentyl)cyclohexane (2,000 grams, 4.1 moles), ethanol (546.8 grams, 11.8 moles) and sodium ethoxide in ethanol (108 grams of a 21% sodium ethoxide in ethanol). The pH of the reaction mixture was about 8. The reaction mixture was heated to 88° C. for 24 hours to remove the ethyl acetate and ethanol from the reaction mixture. Twice ethanol (1 liter) was added to the mixture and the pH of the reaction mixture was increase to about 10 by the addition of 21% sodium ethoxide in ethanol (21 grams) and heated an additional 6.5 hours. The reaction mixture was cooled and then pressure filtered. The reaction mixture was stripped at a temperature less than 95° C. and 1 mmHg pressure. The stripped product was filtered to give (2-triethoxysilylethyl)bis(2-mercaptoethyl)cyclohexane (1398 grams, 3.5 moles, 86% yield).

The product, (2-triethoxysilylethyl)-bis-(7-triethoxysilyl-3,4-dithiaheptyl)cyclohexane, related oligomers and polysulfides, and bis-(3-triethoxysilylpropyl)polysulfide mixture, was prepared by reacting the dimercaptan silane with base, sulfur and 3-chloropropyltriethoxysilane. Into a 3 liter, round bottom flask equipped with a mechanical stirrer, temperature probe/controller, heating mantle, addition funnel, distilling head and Friedrich condenser, and nitorgen inlet was charged (2-triethoxysilylethyl)-bis-(2-mercaptoethyl)cyclohexane (504.3 grams, 1.28 moles). With rapid stirring, a solution of 21% sodium ethoxide in ethanol (829 grams, 2.56 moles), an additional 150 grams of ethanol and sulfur (sublimed powder form Aldrich Chemical, 86.4 grams, 2.7 moles). The solution was refluxed 3.5 hours and then 3-chloropropyltriethoxysilane (616.5 grams, 2.56 moles) over a period of 1.5 hours and then refluxed 17.5 hours. The solution was cooled and pressure filtered through a 2 micron and then a 0.1 micron filter. The filtrate was then stripped at 60° C. and 9 mmHg to remove the ethanol. The product (1027 grams) was analyzed by HPLC and the chromatogram is shown in FIG. 1.

One isomer of (2-triethoxysilylethyl)-bis-(7-triethoxysilyl-3,4-dithiaheptyl)cyclohexane has the following structure:

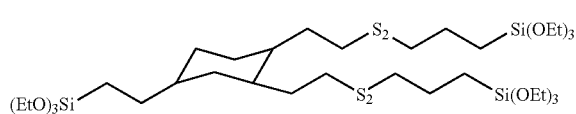

Example 2

Preparation of (2-triethoxysilylethyl)-bis-(9-triethoxysilyl-3,4,5,6-tetrathianonyl)cyclohexane The dimercaptan silane intermediate, (2-triethoxysilylethyl)bis(2-mercaptoethyl)cyclohexane, was prepared by the procedure described in Example 1.

The product, (2-triethoxysilylethyl)-bis-(9-triethoxysilyl-3,4,5,6-tetrathianontyl)cyclohexane related oligomers and polysulfides, and bis-(triethoxysilylpropyl)polysulfide mixture, was prepared by reacting the dimercaptan silane with base, sulfur and 3-chloropropyltriethoxysilane. Into a 5 liter, round bottom flask equipped with a mechanical stirrer, temperature probe/controller, heating mantle, addition funnel, distilling head and Friedrich condenser, and nitorgen inlet was charged (2-triethoxysilylethyl)-bis-(2-mercaptoethyl) cyclohexane (596.3 grams, 1.5 moles). With rapid stirring, a solution of 21% sodium ethoxide in ethanol (979.0 grams, 3.0 moles), an additional 600 grams of ethanol and sulfur (sublimed powder form Aldrich Chemical, 290.0 grams, 9.1 moles). The solution was refluxed overnight and then 3-chloropropyltriethoxysilane (740.0 grams, 3.07 moles) was added and refluxed for 16 hours. The solution was cooled and pressure filtered through a 0.1 micron filter. The filtrate was then stripped using a Rotavapor to remove the ethanol. The product (1,375 grams) was analyzed by HPLC, NMR and GC.

One isomer of (2-triethoxysilylethyl)-bis-(9-triethoxysilyl-3,4,5,6-tetrathianontyl)cyclohexane has the following structure:

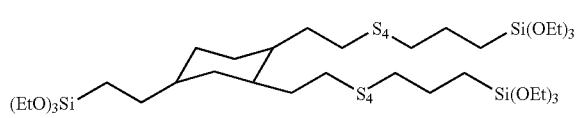

Comparative Example A-E, Examples 3-7

The Use of Silanes in Low Rolling Resistant Tire Tread Formulation

A model low rolling resistance passenger tire tread formulation as described in Table 1 and a mix procedure were used to evaluate representative examples of the silanes of the present invention. The silane in Example 2 was mixed as follows in a "B" BANBURY® (Farrell Corp.) mixer with a 103 cu. in. (1690 cc) chamber volume. The mixing of the rubber was done in two steps. The mixer was turned on with the mixer at 80 rpm and the cooling water at 71° C. The rubber polymers were added to the mixer and ram down mixed for 30 seconds. The silica and the other ingredients in Masterbatch of Table 1 except for the silane and the oils were added to the mixer and ram down mixed for 60 seconds. The mixer speed was reduced to 35 rpm and then the silane and oils of the Materbatch were added to the mixer and ram down for 60 seconds. The mixer throat was dusted down and the ingredients ram down mixed until the temperature reached 149° C. The ingredients were then mixed for an addition 3 minutes and 30 seconds. The mixer speed was adjusted to hold the temperature between 152 and 157° C. The rubber was dumped (removed from the mixer), a sheet was formed on a roll mill set at about 85° to 88° C., and then allowed to cool to ambient temperature.

In the second step, Masterbatch was recharged into the mixer. The mixer's speed was 80 rpm, the cooling water was set at 71° C. and the batch pressure was set at 6 MPa. The Masterbatch was ram down mixed for 30 seconds and then the temperature of the Masterbatch was brought up to 149° C., and then the mixer's speed was reduce to 32 rpm. The rubber was mixed for 3 minutes and 20 seconds at temperatures between 152 and 157° C. After mixing, the rubber was dumped (removed from the mixer), a sheet was formed on a roll mill set at about 85° to 88° C., and then allowed to cool to ambient temperature.

The rubber Masterbatch and the curatives were mixed on a 15 cm×33 cm two roll mill that was heated to between 48° and 52° C. The sulfur and accelerators were added to the rubber (Masterbatch) and thoroughly mixed on the roll mill and allowed to form a sheet. The sheet was cooled to ambient conditions for 24 hours before it was cured. The curing condition was 160° C. for 20 minutes. Silane from Example 2 was compounded into the tire tread formulation according to the above procedure. The performance of the silane prepared in Examples 2 was compared to the performance of silanes which are practiced in the prior art, bis-(3-triethoxysilyl-1-propyl)disulfide (TESPD), and propyltriethoxysilane, Comparative Examples A-E. The test procedures were described in the following ASTM methods:

| | |
|---|---|
| Mooney Scorch | ASTM D1646 |
| Mooney Viscosity | ASTM D1646 |
| Oscillating Disc Rheometer (ODR) | ASTM D2084 |
| Storage Modulus, Loss Modulus, Tensile and Elongation | ASTM D412 and D224 |
| DIN Abrasion | DIN Procedure 53516 |
| Heat Buildup | ASTM D623 |
| Percent Permanent Set | ASTM D623 |
| Shore A Hardness | ASTM D2240 |

The results of this procedure are tabulated below in Table 1.

Table 1, listed in Examples 3-7, presents the performance parameters of hydrocarbon core polysulfide silanes of the present invention, TESPD, and propyltriethoxysilane. The physical properties of the rubber compounded with silane from Example 2 are consistently and substantially higher than the control silanes.

The silated core polysulfide silanes of the present invention impart superior performance to silica-filled elastomer compositions, including better coupling of the silica to the rubber, as illustrated by the higher reinforcement index. The better reinforcing index translate into performance improvements for the elastomer compositions and articles manufactured from these elastomers.

TABLE 1

| Ingredients | Units | Comp. Ex. A | Example 3 | Comp. Ex B | Example 4 | Comp. Ex C | Comp. Ex. D | Example 5 | Comp. Ex. E | Example 6 | Example 7 |
|---|---|---|---|---|---|---|---|---|---|---|---|
| Masterbatch | | | | | | | | | | | |
| SMR-10, natural rubber | phr | 10.00 | 10.00 | 10.00 | 10.00 | 10.00 | 10.00 | 10.00 | 10.00 | 10.00 | 10.00 |
| Budene 1207, polybutadiene | phr | 35.00 | 35.00 | 35.00 | 35.00 | 35.00 | 35.00 | 35.00 | 35.00 | 35.00 | 35.00 |
| Buna VSL 5025-1, oil-ext. sSBR | phr | 75.63 | 75.63 | 75.63 | 75.63 | 75.63 | 75.63 | 75.63 | 75.63 | 75.63 | 75.63 |
| N339, carbon black | phr | 12.00 | 12.00 | 12.00 | 12.00 | 12.00 | 12.00 | 12.00 | 12.00 | 12.00 | 12.00 |
| Ultrasil VN3 GR, silica | phr | 85.00 | 85.00 | 85.00 | 85.00 | 85.00 | 85.00 | 85.00 | 85.00 | 85.00 | 85.00 |
| Sundex 8125TN, process oil. | phr | 6.37 | 6.37 | 6.37 | 6.37 | 6.37 | 6.37 | 6.37 | 6.37 | 6.37 | 6.37 |
| Erucical H102, rapeseed oil | phr | 5.00 | 5.00 | 5.00 | 5.00 | 5.00 | 5.00 | 5.00 | 5.00 | 5.00 | 5.00 |
| Flexzone 7P, antiozonant | phr | 2.00 | 2.00 | 2.00 | 2.00 | 2.00 | 2.00 | 2.00 | 2.00 | 2.00 | 2.00 |
| TMQ | phr | 2.00 | 2.00 | 2.00 | 2.00 | 2.00 | 2.00 | 2.00 | 2.00 | 2.00 | 2.00 |
| Sunproof Improved, wax | phr | 2.50 | 2.50 | 2.50 | 2.50 | 2.50 | 2.50 | 2.50 | 2.50 | 2.50 | 2.50 |
| Kadox 720C, zinc oxide | phr | 2.50 | 2.50 | 2.50 | 2.50 | 2.50 | 2.50 | 2.50 | 2.50 | 2.50 | 2.50 |
| Industrene R, stearic acid | phr | 1.00 | 1.00 | 1.00 | 1.00 | 1.00 | 1.00 | 1.00 | 1.00 | 1.00 | 1.00 |
| Aktiplast ST, disperser | phr | 4.00 | 4.00 | 4.00 | 4.00 | 4.00 | 4.00 | 4.00 | 4.00 | 4.00 | 4.00 |
| Silane TESPD | phr | 6.00 | | 6.00 | | 6 | | | 6 | | |
| Silane, propyl-triethoxysilane | phr | — | | — | | — | 5.22 | | | | |
| Silane Example 2 | phr | — | 8.50 | | 8.50 | | | 8.5 | | 8.5 | 8.5 |
| Catalysts | | | | | | | | | | | |
| cyclohexyl amine | phr | 0.75 | 0.75 | 0.75 | 0.75 | 0.75 | 0.75 | 0.75 | 0.75 | 0.75 | 0.75 |
| Naugex MBT | phr | | | | | | | | 0.1 | 0.1 | 0.1 |
| MBTS | phr | | | | | | | | 1.26 | 1.26 | 1.26 |
| TMTD | phr | | | | | | 1.82 | 1.82 | 1.82 | | |
| TMTM | phr | | | 1.58 | 1.58 | | | | | | |
| Diphenyl guanidine | phr | | | | | | | | 2 | 2 | 2 |
| Propyl zithate | phr | 2.54 | 2.54 | | | | | | | | |
| Rubbermakers sulfur 167 | phr | | | | | | | | 2 | 2 | |
| total | phr | 252.29 | 254.78 | 251.32 | 253.82 | 251.56 | 250.78 | 254.06 | 255.10 | 257.60 | 255.60 |
| Specific Gravity | g/cm3 | 1.20 | 1.21 | 1.20 | 1.20 | 1.202 | 1.199 | 1.204 | 1.207 | 1.208 | 1.204 |
| Physical Properties | | | | | | | | | | | |
| Mooney Viscosity at 100 Celsius ML1 + 3 | mooney units | 71.2 | | 72.4 | 77.1 | 72.2 | 110.5 | 95.6 | 68.9 | 82.8 | 76.1 |
| Minimum Torque (Mooney Low) | dNm | 2.8 | 6.33 | 2.99 | 2.9 | 3.2 | 11.7 | 3.62 | 2.7 | 3.33 | 2.87 |
| Maximum Torque (Mooney High | dNm | 6.45 | 12.41 | 8 | 14.57 | 12.27 | 16.77 | 19 | 19.01 | 24.72 | 15.52 |
| Torque (Max-Min) | dNm | 3.65 | 6.08 | 5.01 | 11.67 | 9.07 | 5.07 | 15.38 | 16.31 | 21.39 | 12.65 |
| 1.13 DNM RISE | min | 0.82 | 0.51 | 0.54 | 0.6 | 0.47 | 0.11 | 0.44 | 0.52 | 0.38 | 0.57 |
| 2.26 DNM RISE | min | 3.53 | 1.27 | 1.32 | 0.99 | 0.84 | 0.15 | 0.61 | 0.68 | 0.51 | 1 |
| Cure, 160 Celsius for 20 minutes | | | | | | | | | | | |
| T-10 | min | 0.39 | 0.39 | 0.36 | 0.67 | 0.44 | 0.11 | 0.53 | 0.63 | 0.52 | 0.67 |
| T-40 | min | 1.55 | 2.07 | 1.33 | 1.92 | 1.36 | 0.52 | 1.3 | 1.2 | 1.24 | 3.31 |
| T-95 | min | 24.59 | 26.48 | 23.53 | 22.36 | 18.69 | 4.64 | 18.85 | 13.71 | 19.61 | 21.75 |
| cure time | min | 20 | 20 | 20 | 20 | 20 | 20 | 20 | 20 | 20 | 20 |
| 50% Modulus | MPa | 0.4 | 0.733 | 0.4 | 0.9 | 0.7 | 0.5 | 1.367 | 1.3 | 1.767 | 0.967 |
| 100% Modulus | MPa | 0.4 | 1 | 0.4 | 1.3 | 0.9 | 0.5 | 2.4 | 2.3 | 3.367 | 1.367 |
| 300% Modulus | MPa | 0.5 | 3.2 | 0.5 | 4.767 | 2.7 | 0.7 | 11.93 | 10.03 | 14.8 | 5.133 |
| Reinforcement Index | | 1.3 | 3.2 | 1.3 | 3.7 | 3 | 1.4 | 5 | 4.4 | 4.4 | 3.8 |
| Tensile | MPa | 0.7 | 4.467 | 0.7 | 14.13 | 11.47 | 3.3 | 16.73 | 16.17 | 16.03 | 13.77 |
| Elongation | % | 849.2 | 440.3 | 875.8 | 666.5 | 887.9 | 1280 | 414.9 | 477.5 | 349.6 | 635.6 |
| M300-M100 | | 0.1 | 2.2 | 0.1 | 3.5 | 1.8 | 0.2 | 9.5 | 7.7 | 11.4 | 3.8 |
| Durometer Shore "A" | shore A | 36.7 | 51.7 | 41.1 | 59.3 | 54.8 | 49.6 | 67.4 | 67.9 | 70.9 | 59.8 |
| Zwick Rebound, Room Temperat | percent | 23.8 | 30.9 | 22.3 | 32 | 28.8 | 24.2 | 36.4 | 28.9 | 33.8 | 30.4 |

TABLE 1-continued

| Ingredients | Units | Comp. Ex. A | Example 3 | Comp. Ex B | Example 4 | Comp. Ex C | Comp. Ex. D | Example 5 | Comp. Ex. E | Example 6 | Example 7 |
|---|---|---|---|---|---|---|---|---|---|---|---|
| Zwick Rebound, 70 Celsius | percent | 26.4 | 37.5 | 25.4 | 40.4 | 36.4 | 27.2 | 49.2 | 45.2 | 52.4 | 41.9 |
| Delta Rebound, 70 C.-RT | percent | 2.6 | 6.6 | 3.1 | 10.4 | 7.6 | 3 | 12.8 | 16.3 | 18.6 | 11.5 |
| energy at Break | | 4.6 | 10.15 | 4.65 | 41 | 45.69 | 21.25 | 31.19 | 36.23 | 27.03 | 38.6 |

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

The invention claimed is:

1. A silated core polysulfide of the general formula $$[Y^1R^1S_x-]_m[G^1(R^2SiX^1X^2X^3)_a]_n[G^2]_o[R^3Y^2]_p$$

wherein:
each occurrence of $G^1$ is independently selected from a polyvalent hydrocarbon species having from 3 to about 30 carbon atoms containing a polysulfide group represented by the general formula:

$$[(CH_2)_b-]_cR^4[-(CH_2)_dS_x-]_e;$$

each occurrence of $G^2$ is independently selected from a polyvalent hydrocarbon species of 3 to about 30 carbon atoms containing a polysulfide group represented by the general formula:

$$[(CH_2)_b-]_cR^5[-(CH_2)_dS_x-]_e;$$

each occurrence of $R^1$ and $R^3$ is independently selected from a divalent hydrocarbon fragment having from 1 to about 20 carbon atoms;
each occurrence of $Y^1$ and $Y^2$ is independently selected from the group consisting of silyl ($-SiX^1X^2X^3$), hydrogen, carboxylic acid and ester group ($-C(=O)OR^6$) wherein $R^6$ is a monovalent hydrocarbon group having from 1 to 20 carbon atoms;
each occurrence of $R^2$ is a straight chain hydrocarbon represented by $-(CH_2)_f-$;
each occurrence of $R^4$ is independently selected from a polyvalent hydrocarbon fragment of 1 to about 28 carbon atoms;
each occurrence of $R^5$ is independently selected from a polyvalent hydrocarbon fragment of 1 to about 28 carbon atoms;
each occurrence of $X^1$ is independently selected from the group consisting of —Cl, —Br, —OH, —$OR^6$, and $R^6C(=O)O-$, wherein $R^6$ is a monovalent hydrocarbon group having from 1 to 20 carbon atoms;
each occurrence of $X^2$ and $X^3$ is independently selected from the group consisting of hydrogen, $R^6$, wherein $R^6$ is a monovalent hydrocarbon group having from 1 to 20 carbon atoms, $X^1$, wherein $X^1$ is independently selected from the group consisting of —Cl, —Br, —OH, —$OR^6$, and $R^6C(=O)O-$, wherein $R^6$ is a monovalent hydrocarbon group having from 1 to 20 carbon atoms, and —OSi containing groups that result from the condensation of silanols;
each occurrence of the subscripts, a, b, c, d, e, f, m, n, o, p, and x, is independently given by: a is 1 to 2; b and d are 1 to 3; c and e are 1; f is 0 to 3; m and p are 1; n is 1 to 10; o is 0 to 1; and x is 2 to 4.

2. The silated core polysulfide of claim 1 wherein each $R^1$, $R^3$ and $R^6$ is independently a branched or straight chain alkyl, alkenyl, alkynyl, aryl or aralkyl group.

3. The silated core polysulfide of claim 1 wherein each $R^4$ and $R^5$ is independently a cyclic, branched or straight chain alkyl, alkenyl, alkynyl, aryl, or aralkyl group in which a+c+e−1 hydrogens have been replaced.

4. The silated core polysulfide of claim 3 wherein the alkyl, alkynyl, aryl, aralkyl and arenyl of $R^4$ or $R^5$ in which a+c+e−1 hydrogens have been replaced is derived from the group consisting of methyl, ethyl, propyl, and isobutyl, vinyl, propenyl, allyl, methallyl, ethylidenyl norbornane, ethylidene norbornyl, ethylidenyl norbornene, ethylidene norbornenyl, acetylenyl, and propargyl, methylacetylenyl, phenyl, naphthalenyl, benzyl, phenethyl, tolyl, xylyl, norbornyl, norbornenyl, ethylnorbornyl, ethylnorbornenyl, cyclohexyl, ethylcyclohexyl, ethylcyclohexenyl, cyclohexylcyclohexyl, and cyclododecatrienyl.

5. The silated core polysulfide of claim 1 wherein each $R^4$ and $R^5$ is independently a polyvalent hydrocarbon fragment selected from the group consisting of bicyclic, tricyclic, higher cyclic structures and cyclic structures substituted with alkyl, alkenyl, and/or alkynyl groups.

6. The silated core polysulfide of claim 1 wherein $X^1$ is selected from the group consisting of methoxy, ethoxy, propoxy, isopropoxy, butoxy, phenoxy, benzyloxy, hydroxy, chloro, and acetoxy.

7. The silated core polysulfide of claim 1 wherein each $X^2$ and $X^3$ is independently selected from the group consisting of methoxy, ethoxy, propoxy, isopropoxy, butoxy, phenoxy, benzyloxy, hydroxy, chloro, acetoxy, hydrogen, methyl, ethyl, propyl, isopropyl, sec-butyl, phenyl, vinyl, cyclohexyl, butyl, hexyl, octyl, lauryl, and octadecyl.

8. The silated core polysulfide of claim 1 wherein each $R^1$ and $R^3$ is independently a divalent hydrocarbon fragment derived from methallyl chloride, divinylbenzene, diallylether, butadiene, piperylene, isoprene, diradicals, limonene, monovinyl-containing structures derived from trivinylcyclohexane, monounsaturated structures derived from myrcene containing a trisubstituted C=C, monounsaturated structures derived from myrcene lacking a trisubstituted C=C, and mixtures thereof.

9. The silated core polysulfide of claim 1 wherein each $G^1$ and $G^2$ is independently a polyvalent hydrocarbon species containing a polysulfide group derived from nonconjugated terminal diolefins.

10. The silated core polysulfide of claim 1 wherein each $G^1$ and $G^2$ is independently a polyvalent hydrocarbon species containing a polysulfide group derived from the group consisting of $-CH_2(CH_2)_{q+1}CH(CH_2)-$, $-CH(CH_3)(CH_2)_qCH(CH_2-)_2$, wherein q is zero to 20.

11. The silated core polysulfide of claim 1 wherein each $G^1$ and $G^2$ is independently a polyvalent hydrocarbon species containing a polysulfide group derived from divinylbenzene, diallylether, butadiene, piperylene, isoprene, trivinylcyclohexane, myrcene, and mixture thereof.

12. The silated core polysulfide of claim 1 wherein each $R^1$ and $R^3$ is independently a divalent hydrocarbon fragment having from 1 to about 5 carbon atoms.

13. The silated core polysulfide of claim 1 wherein $X^1$ is independently selected from the group consisting of hydrolysable —OH, and —$OR^6$, wherein $R^6$ is a monovalent hydrocarbon group having from 1 to 5 carbon atoms.

14. A composition comprising from about 30 to about 99 weight percent of the silated core polysulfide of claim 1 and about 70 to about 1 weight percent of a silane of the general formula:

$$X^1X^2X^3SiR^1S_xR^3SiX^1X^2X^3$$

wherein each occurrence of $R^1$ and $R^3$ is independently selected from a divalent hydrocarbon fragment having from 1 to about 20 carbon atoms;

each occurrence of $X^1$ is independently selected from the group consisting of —Cl, —Br, —OH, —$OR^6$, and $R^6C(=O)O—$, wherein $R^6$ is a monovalent hydrocarbon group having from 1 to 20 carbon atoms;

each occurrence of $X^2$ and $X^3$ is independently selected from the group consisting of hydrogen, $R^6$, $X^1$, and —OSi containing groups that result from the condensation of silanols;

and x is 1 to about 10.

15. The composition of claim 14 wherein the silane is selected from the group consisting of bis-(3-triethoxysilylpropyl) disulfide; bis-(3-triethoxysilylpropyl) trisulfide; bis-(3-triethoxysilylpropyl) tetrasulfide; bis-(3-triethoxysilylpropyl) pentasulfide; bis-(3-diethoxymethylsilylpropyl) disulfide; bis-(3-ethoxydimethylsilylpropyl) disulfide; bis-(triethoxysilylmethyl) disulfide; bis-(4-triethoxysilylbenzyl) disulfide, bis-(3-triethoxysilylphenyl) disulfide, and mixtures thereof.

16. A process for making a silated core polysulfide according to claim 1 which comprises:
(a) reacting a hydrosilane having the structure, HSi($X^1X^2X^3$), with a hydrocarbon containing at least one reactive double bonds to produce an intermediate product;
(b) reacting the intermediate product from step (a) with a sulfuring agent, selected from the group $R^6C(=O)SH$, wherein $R^6$ is a monovalent hydrocarbon group having from 1 to 20 carbon atoms, in the presence of a free radical agent;
(c) deblocking the mercapto group on the product in step (b) using a proton donator;
(d) reacting the intermediate mercaptan in step (c) with a mixture of base and sulfur;
(e) reacting the intermediate in step (d) with a substituted or unsubstituted hydrocarbon containing a leaving group selected from the group consisting of chlorine, bromine or iodine and mixtures thereof.

17. A rubber composition comprising:
(a) silated core polysulfide of the general formula $$[Y^1R^1S_x—]_m[G^1(R^2SiX^1X^2X^3)_a]_n[G^2]_o[R^3Y^2]_p;$$

wherein each occurrence of $G^1$ is independently selected from a polyvalent hydrocarbon species having from 3 to about 30 carbon atoms containing a polysulfide group represented by the general formula:

$$[(CH_2)_b—]_cR^4[—(CH_2)_dS_x—]_e;$$

each occurrence of $G^2$ is independently selected from a polyvalent hydrocarbon species of 3 to about 30 carbon atoms containing a polysulfide group represented by the general formula:

$$[(CH_2)_b—]_cR^5[—(CH_2)_dS_x—]_e;$$

each occurrence of $R^1$ and $R^3$ is independently selected from a divalent hydrocarbon fragment having from 1 to about 20 carbon atoms;

each occurrence of $Y^1$ and $Y^2$ is independently selected from consisting of silyl (—$SiX^1X^2X^3$), carboxylic acid, ester (—C(=O)$OR^6$) wherein $R^6$ is a monovalent hydrocarbon group having from 1 to 20 carbon atoms, hydroxyl, hydrogen;

each occurrence of $R^2$ is a straight chain hydrocarbon represented by —$(CH_2)_f$—;

each occurrence of $R^4$ is independently a polyvalent hydrocarbon fragment of 1 to about 28 carbon atoms;

each occurrence of $R^5$ is independently a polyvalent hydrocarbon fragment of 1 to about 28 carbon atoms;

each occurrence of $X^1$ is independently selected from the group consisting of —Cl, —Br, —OH, —$OR^6$, and $R^6C(=O)O—$, wherein $R^6$ is a monovalent hydrocarbon group having from 1 to 20 carbon atoms;

each occurrence of $X^2$ and $X^3$ is independently selected from the group consisting of hydrogen, $R^6$, wherein $R^6$ is a monovalent hydrocarbon group having from 1 to 20 carbon atoms, $X^1$, wherein $X^1$ is independently selected from the group consisting of —Cl, —Br, —OH, —$OR^6$, and $R^6C(=O)O—$, wherein $R^6$ is a monovalent hydrocarbon group having from 1 to 20 carbon atoms, and —OSi containing groups that result from the condensation of silanols;

each occurrence of the subscripts, a, b, c, d, e, f, m, n, o, p, and x, is independently given by a is 1 to 2; b is 1 to 3; c is 1; d is 1 to 3; e is 1; f is 0 to 3; m and p are 1; n is 1 to 10; o is 0 to 1; and x is 2 to 4;

(b) inorganic filler; and,
(c) rubber.

18. The rubber composition of claim 17, further comprising (d) curative and, optionally, at least one other additive selected from the group consisting of sulfur compounds, activators, retarders, accelerators, processing additives, oils, plasticizers, tackifying resins, silicas, fillers, pigments, fatty acids, zinc oxide, waxes, antioxidants and antiozonants, peptizing agents, reinforcing materials, and mixtures thereof.

19. The rubber composition of claim 17, wherein the rubber component is at least one sulfur vulcanizable rubber selected from the group consisting of conjugated diene homopolymers and copolymers, copolymers of at least one conjugated diene and aromatic vinyl compound and mixtures thereof.

20. The rubber composition of claim 19, wherein the rubber component is styrene/butadiene rubber containing from about 5 to about 50 percent vinyl content.

21. The rubber composition of claim 19, wherein the rubber component is derived from a conjugated diene selected from the group consisting of isoprene, 1,3-butadiene, styrene, and alpha methyl styrene, and mixture thereof.

22. The rubber composition of claim 19 wherein the rubber component is styrene/butadiene having a styrene content of about 20 to about 28 weight percent.

23. The rubber composition of claim 17, wherein the rubber component is at least one natural rubber, or emulsion polymerization derived rubber, or a solvent polymerization derived rubber.

24. The rubber composition of claim 17, wherein the rubber is selected from the group consisting of cis-1,4-polyisoprene rubber, emulsion polymerization prepared styrene/butadiene copolymer rubber, organic solution polymerization prepared styrene/butadiene rubber, 3,4-polyisoprene rubber, isoprene/butadiene rubber, styrene/isoprene/butadiene terpolymer rubber, cis-1,4-polybutadiene, medium vinyl polybutadiene rubber, wherein the medium vinyl polybutadiene rubber has about 35 to 50 weight percent vinyl, high vinyl polybutadiene rubber wherein the high vinyl polybutadiene rubber has about 50 to 75 weight percent vinyl, styrene/isoprene copolymers, emulsion polymerization prepared styrene/butadiene/acrylonitrile terpolymer rubber and butadiene/acrylonitrile copolymer rubber.

25. The rubber composition of claim 17 wherein the silated core polysulfide is selected from the group consisting of 2-triethoxysilyl-1,3-bis-(3-triethoxysilyl-1-propyltetrathia) propane, 4-(2-triethoxysilyl-1-ethyl)-1,2-bis-(13-triethoxysilyl-3,4,5,6-tetrathiamidecyl)cyclohexane; 4-(2-triethoxysilyl-1-ethyl)-1,2-bis-(13-triethoxysilyl-3,4,5,6-tetrathiamidecyl)cyclohexane; 4-(2-diethoxymethylsilyl-1-ethyl)-1,2-bis-(13-triethoxysilyl-3,4,5,6-tetrathiamidecyl)cyclohexane; 4-(2-triethoxysilyl-1-ethyl)-1,2-bis-(10-triethoxysilyl-3,4,5,6,7-pentathiadecyl)cyclohexane; 1-(2-triethoxysilyl-1-ethyl)-2,4-bis-(10-triethoxysilyl-3,4,5,6,7-pentathiadecyl)cyclohexane; 4-(2-triethoxysilyl-1-ethyl)-1,2-bis-(9-triethoxysilyl-3,4,5,6-tetrathianonyl)cyclohexane; 1-(2-triethoxysilyl-1-ethyl)-2,4-bis-(9-triethoxysilyl-3,4,5,6-tetrathianonyl)cyclohexane; 2-(2-triethoxysilyl-1-ethyl)-1,4-bis-(9-triethoxysilyl-3,4,5,6-tetrathianonyl)cyclohexane; 4-(2-triethoxysilyl-1-ethyl)-1,2-bis-(8-triethoxysilyl-3,4,5-trithiaoctyl)cyclohexane; 1-(2-triethoxysilyl-1-ethyl)-2,4-bis-(8-triethoxysilyl-3,4,5-trithiaoctyl)cyclohexane; 2-(2-triethoxysilyl-1-ethyl)-1,4-bis-(8-triethoxysilyl-3,4,5-trithiaoctyl)cyclohexane; 4-(2-triethoxysilyl-1-ethyl)-1,2-bis-(7-triethoxysilyl-3,4-dithiaheptyl)cyclohexane; 2-(2-triethoxysilyl-1-ethyl)-1,4-bis-(7-triethoxysilyl-3,4-dithiaheptyl)cyclohexane; 2-(2-triethoxysilyl-1-ethyl)-1-(7-triethoxysilyl-3,4-dithiaheptyl)-2-(8-triethoxysilyl-3,4,5-trithiaoctyl)cyclohexane; -(2-triethoxysilyl-1-ethyl)-1,2-bis-(9-triethoxysilyl-3,4,5,6-tetrathianonyl)benzene; bis-[2-[4-(2-triethoxysilyl-1-ethyl)-2-(9-triethoxysilyl-3,4,5,6-tetrathianonyl)cyclohexyl]ethyl]tetrasulfide; bis-[2-[4-(2-triethoxysilyl-1-ethyl)-2-(9-triethoxysilyl-3,4,5,6-tetrathianonyl)cyclohexyl]ethyl]trisulfide; bis-[2-[4-(2-tiethoxysilyl-1-ethyl)-2-(9-triethoxysilyl-3,4,5,6-tetrathianonyl)cyclohexyl]ethyl]disulfide; bis-[2-[4-(2-triethoxysilyl-1-ethyl)-2-(7-triethoxysilyl-3,4-dithiaheptyl) cyclohexyl]ethyl]disulfide; bis-2-[4-(2-triethoxysilyl-1-ethyl)-2-(7-triethoxysilyl-3,4-dithiaheptyl)cyclohexyl] ethyl]trisulfide; bis-[2-[4-(2-triethoxysilyl-1-ethyl)-2-(7-triethoxysilyl-3,4-dithiaheptyl)cyclohexyl]ethyl tetrasulfide; bis-[2-[4-(2-triethoxysilyl-1-ethyl)-2-(9-triethoxysilyl-3,4,5,6-tetrathianonyl)phenyl]ethyl]tetrasulfide; bis-2-[4-(2-triethoxysilyl-1-ethyl)-3-bis-(9-triethoxysilyl-3,4,5,6-tetrathianonyl)cyclohexyl]ethyl]trisulfide; bis-[2-[4-(2-diethoxymethylsilyl-1-ethyl)-2-(7-triethoxysilyl-3,4-dithiaheptyl)cyclohexyl]ethyl disulfide and mixtures thereof.

26. The rubber composition of claim 17 further comprising a silane of the general formula:

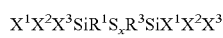

wherein each occurrence of $R^1$ and $R^3$ is independently selected from a divalent hydrocarbon fragment having from 1 to about 20 carbon atoms;

each occurrence of $X^1$ is independently selected from the group consisting of —Cl, —Br, —OH, —$OR^6$, and $R^6C$(=O)O—, wherein $R^6$ is a monovalent hydrocarbon group having from 1 to 20 carbon atoms;

each occurrence of $X^2$ and $X^3$ is independently selected from the group consisting of hydrogen, $R^6$, $X^1$, and —OSi containing groups that result from the condensation of silanols;

and x is 1 to about 10.

27. The rubber composition of claim 26, wherein the silane is selected from the group consisting of bis-(3-triethoxysilylpropyl) disulfide; bis-(3-triethoxysilylpropyl) trisulfide; bis-(3-triethoxysilylpropyl) tetrasulfide; bis-(3-triethoxysilylpropyl) pentasulfide; bis-(3-diethoxymethylsilylpropyl) disulfide; bis-(3-ethoxydimethylsilylpropyl) disulfide; bis-(triethoxysilylmethyl) disulfide; bis-(4-triethoxysilylbenzyl) disulfide, bis-(3-triethoxysilylphenyl) disulfide, and mixtures thereof.

28. The rubber composition of claim 27, wherein the silated core polysulfide is selected from the group consisting of 2-triethoxysilyl-1,3-bis-(3-triethoxysilyl-1-propyltetrathia)propane, 4-(2-triethoxysilyl-1-ethyl)-1,2-bis-(13-triethoxysilyl-3,4,5,6-tetrathiamidecyl)cyclohexane; 4-(2-triethoxysilyl-1-ethyl)-1,2-bis-(13-triethoxysilyl-3,4,5,6-tetrathiamidecyl)cyclohexane; 4-(2-diethoxymethylsilyl-1-ethyl)-1,2-bis-(13-triethoxysilyl-3,4,5,6-tetrathiamidecyl)cyclohexane; 4-(2-triethoxysilyl-1-ethyl)-1,2-bis-(10-triethoxysilyl-3,4,5,6,7-pentathiadecyl)cyclohexane; 1-(2-triethoxysilyl-1-ethyl)-2,4-bis-(10-triethoxysilyl-3,4,5,6,7-pentathiadecyl)cyclohexane; 4-(2-triethoxysilyl-1-ethyl)-1,2-bis-(9-triethoxysilyl-3,4,5,6-tetrathianonyl)cyclohexane; 1-(2-triethoxysilyl-1-ethyl)-2,4-bis-(9-triethoxysilyl-3,4,5,6-tetrathianonyl)cyclohexane; 2-(2-triethoxysilyl-1-ethyl)-1,4-bis-(9-triethoxysilyl-3,4,5,6-tetrathianonyl)cyclohexane; 4-(2-triethoxysilyl-1-ethyl)-1,2-bis-(8-triethoxysilyl-3,4,5-trithiaoctyl)cyclohexane; 1-(2-triethoxysilyl-1-ethyl)-2,4-bis-(8-triethoxysilyl-3,4,5-trithiaoctyl)cyclohexane; 2-(2-triethoxysilyl-1-ethyl)-1,4-bis-(8-tiethoxysilyl-3,4,5-trithiaoctyl)cyclohexane; 4-(2-triethoxysilyl-1-ethyl)-1,2-bis-(7-triethoxysilyl-3,4-dithiaheptyl)cyclohexane; 2-(2-triethoxysilyl-1-ethyl)-1,4-bis-(7-triethoxysilyl-3,4-dithiaheptyl)cyclohexane; 2-(2-triethoxysilyl-1-ethyl)-1-(7-triethoxysilyl-3,4-dithiaheptyl)-2-(8-triethoxysilyl-3,4,5-trithiaoctyl)cyclohexane, -(2-triethoxysilyl-1-ethyl)-1,2-bis-(9-triethoxysilyl-3,4,5,6-tetrathianonyl)benzene; bis-[2-[4-(2-triethoxysilyl-1-ethyl)-2-(9-triethoxysilyl-3,4,5,6-tetrathianonyl)cyclohexyl]ethyl]tetrasulfide; bis-[2-[4-(2-triethoxysilyl-1-ethyl)-2-(9-triethoxysilyl-3,4,5,6-tetrathianonyl)cyclohexyl]ethyl]trisulfide; bis-[2-[4-(2-triethoxysilyl-1-ethyl)-2-(9-triethoxysilyl-3,4,5,6-tetrathianonyl)cyclohexyl]ethyl]disulfide; bis-[2-[4-(2-triethoxysilyl-1-ethyl)-2-(7-triethoxysilyl-3,4-dithiaheptyl)cyclohexyl]ethyl]disulfide; bis-2-[4-(2-triethoxysilyl-1-ethyl)-2-(7-triethoxysilyl-3,4-dithiaheptyl)cyclohexyl]ethyl]trisulfide; bis-[2-[4-(2-triethoxysilyl-1-ethyl)-2-(7-triethoxysilyl-3,4-dithiaheptyl)cyclohexyl]ethyl tetrasulfide; bis-[2-[4-(2-triethoxysilyl-1-ethyl)-2-(9-triethoxysilyl-3,4,5,6-tetrathianonyl)phenyl]ethyl]tetrasulfide; bis-2-[4-(2-triethoxysilyl-1-ethyl)-3-bis-(9-triethoxysilyl-3,4,5,6-tetrathianonyl)cyclohexyl]ethyl]trisulfide; bis-[2-[4-(2-diethoxymethylsilyl-1-ethyl)-2-(7-triethoxysilyl-3,4-dithiaheptyl)cyclohexyl]ethyl disulfide and mixtures thereof.

* * * * *